(12) United States Patent
Berz

(10) Patent No.: US 11,578,325 B2
(45) Date of Patent: Feb. 14, 2023

(54) METHODS AND FORMULATIONS FOR THE TREATMENT OF OBESITY AND OBESITY-RELATED METABOLIC DISEASES

(71) Applicant: David Berz, Los Angeles, CA (US)

(72) Inventor: David Berz, Los Angeles, CA (US)

(*) Notice: Subject to any disclaimer, the term of this patent is extended or adjusted under 35 U.S.C. 154(b) by 0 days.

(21) Appl. No.: 17/058,033

(22) PCT Filed: May 23, 2019

(86) PCT No.: PCT/US2019/033847
§ 371 (c)(1),
(2) Date: Nov. 23, 2020

(87) PCT Pub. No.: WO2019/226952
PCT Pub. Date: Nov. 28, 2019

(65) Prior Publication Data
US 2021/0198668 A1    Jul. 1, 2021

Related U.S. Application Data

(60) Provisional application No. 62/676,196, filed on May 24, 2018.

(51) Int. Cl.
*C12N 15/113* (2010.01)
*C12Q 1/68* (2018.01)

(52) U.S. Cl.
CPC ........ *C12N 15/113* (2013.01); *C12N 2310/11* (2013.01); *C12N 2320/32* (2013.01); *C12N 2320/35* (2013.01)

(58) Field of Classification Search
None
See application file for complete search history.

(56) References Cited

U.S. PATENT DOCUMENTS

| | | | |
|---|---|---|---|
| 6,268,490 B1 | 7/2001 | Imanishi et al. | C07H 21/00 |
| 6,770,748 B2 | 8/2004 | Imanishi et al. | C07H 21/00 |
| RE44,779 E | 2/2014 | Imanishi et al. | C07H 19/06 |
| 9,566,293 B2 | 2/2017 | Hardee et al. | C07H 21/02 |
| 2009/0099117 A1 | 4/2009 | McSwiggen et al. | A61K 31/7105 |
| 2009/0209625 A1* | 8/2009 | Bhanot | A61P 3/04 435/375 |
| 2012/0129917 A1* | 5/2012 | Collard | C12N 15/113 435/375 |
| 2017/0198032 A1 | 7/2017 | Donovan et al. | C07K 16/22 |
| 2020/0283764 A1* | 9/2020 | Klar | A61P 35/00 |

FOREIGN PATENT DOCUMENTS

| | | | |
|---|---|---|---|
| WO | WO 2018/019748 | 2/2018 | C07H 19/06 |

OTHER PUBLICATIONS

International Search Report and Written Opinion issued in PCT Application No. PCT/US2019/033847 dated Aug. 8, 2019, 7 pgs.
International Preliminary Report on Patentability issued in PCT Application No. PCT/US2019/033847 dated Nov. 24, 2020, 6 pgs.
Martinovich et al., "The potential of antisense oligonucleotide therapies for inherited childhood lung diseases", Molecular and Cellular Pediatrics, vol. 5, No. 3 (2018), 10 pgs.

* cited by examiner

*Primary Examiner* — Sean McGarry
(74) *Attorney, Agent, or Firm* — Hayes Soloway P.C.

(57) ABSTRACT

An oligo- or polynucleotide analogue having one or more structures of the general formula: where B is a pyrimidine or purine nucleic acid base, or an analogue thereof, is used for treating obesity-related metabolic diseases.

10 Claims, 30 Drawing Sheets
(30 of 30 Drawing Sheet(s) Filed in Color)
Specification includes a Sequence Listing.

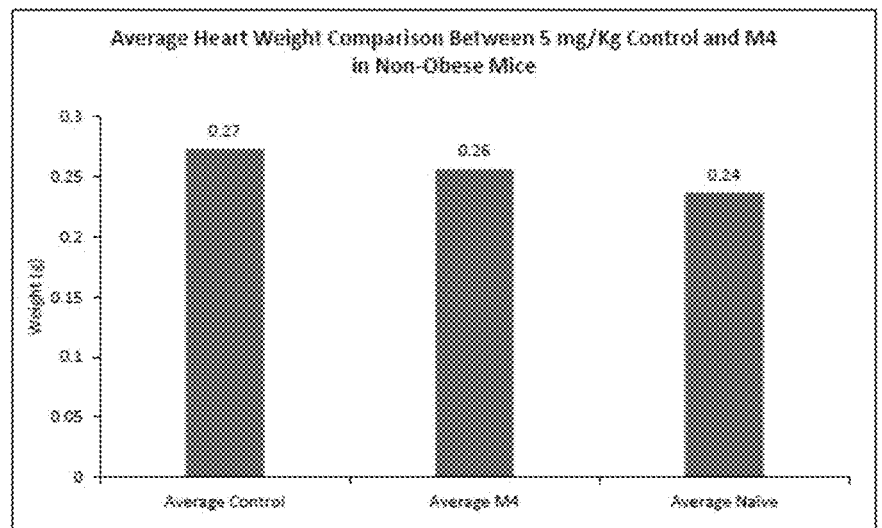
FIG. 6
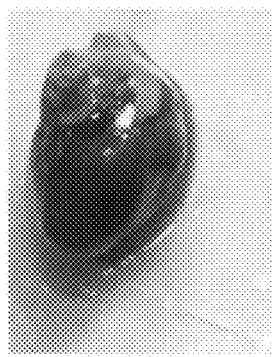   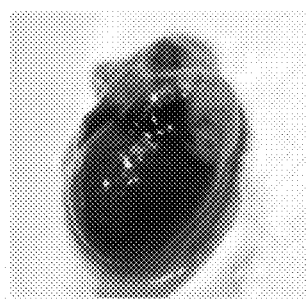   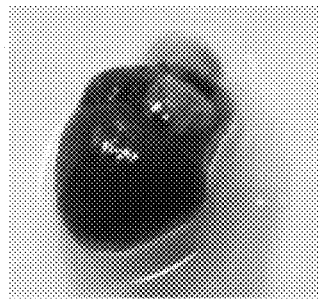
FIG. 7A          FIG. 7B          FIG. 7C

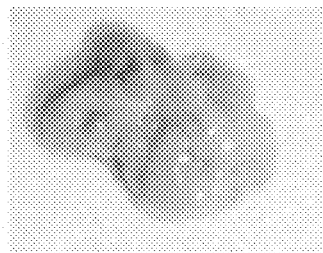
Naïve 203
2.86 g
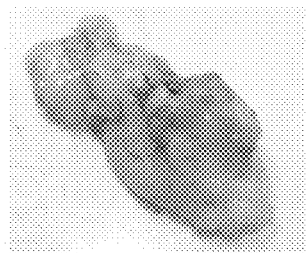
205C
4.40 g
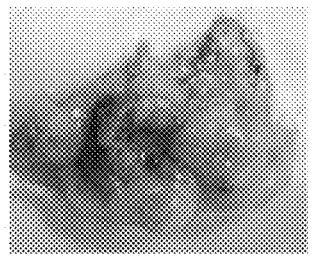
208 M4
4.36 g
FIG. 8A  FIG. 8B  FIG. 8C
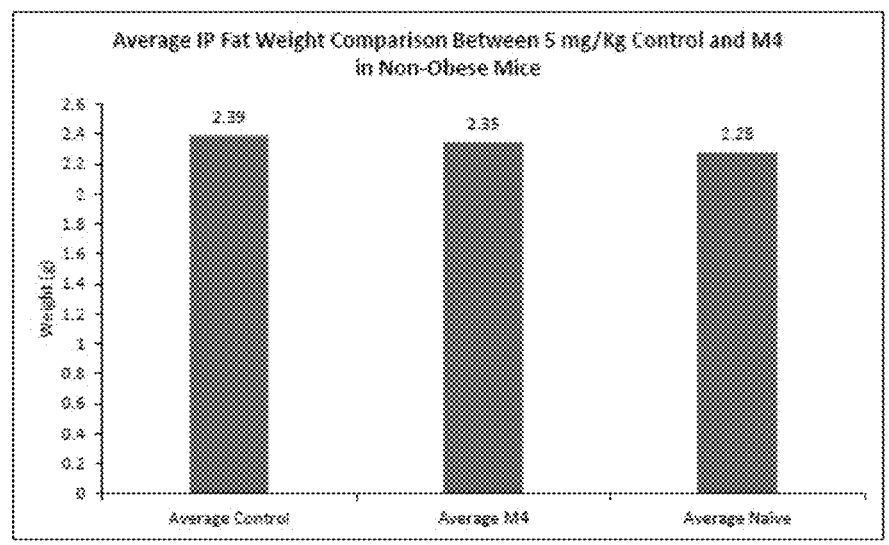
FIG. 9
Naïve 203
2.08 g
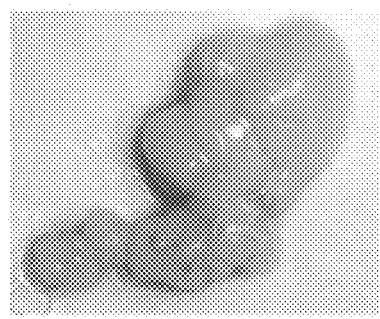
205C
2.63 g
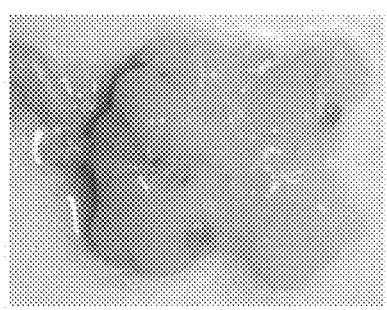
208 M4
2.56 g
FIG. 10A  FIG. 10B  FIG. 10C Naïve 203
0.52 g 205C
0.58 g 208 M4
0.54 g

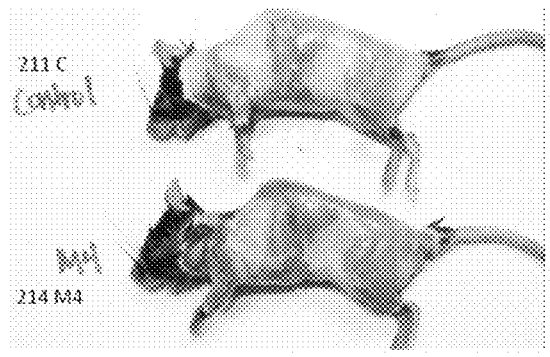
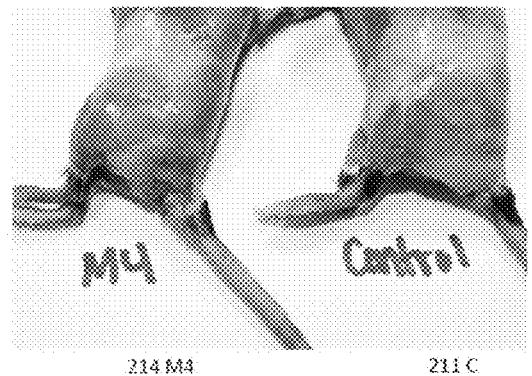
FIG. 15A  FIG. 15B
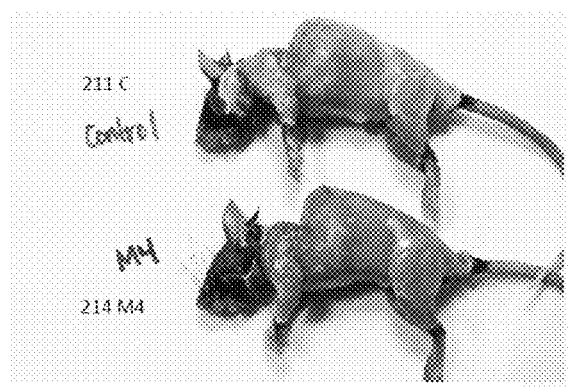
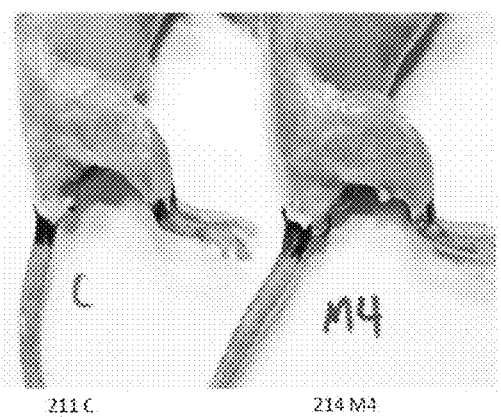
FIG. 16A  FIG. 16B
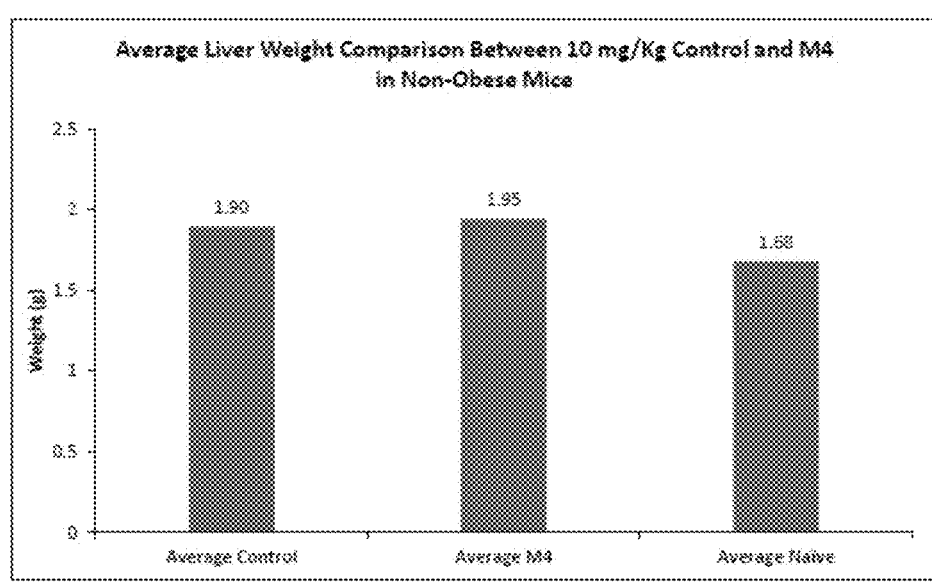
FIG. 17

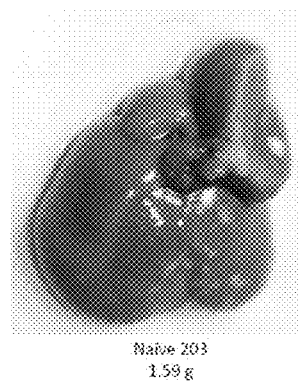
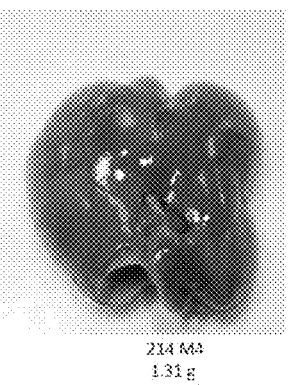
FIG. 18A  FIG. 18B  FIG. 18C
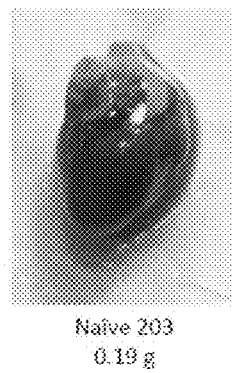
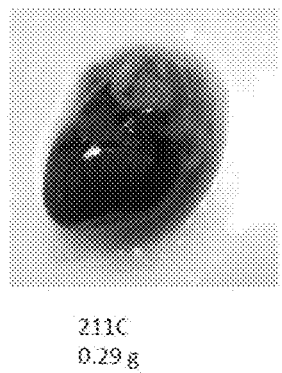
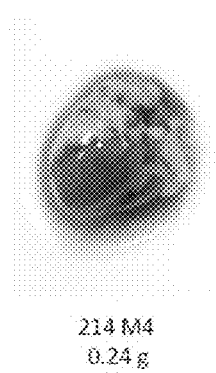
FIG. 19A  FIG. 19B  FIG. 19C
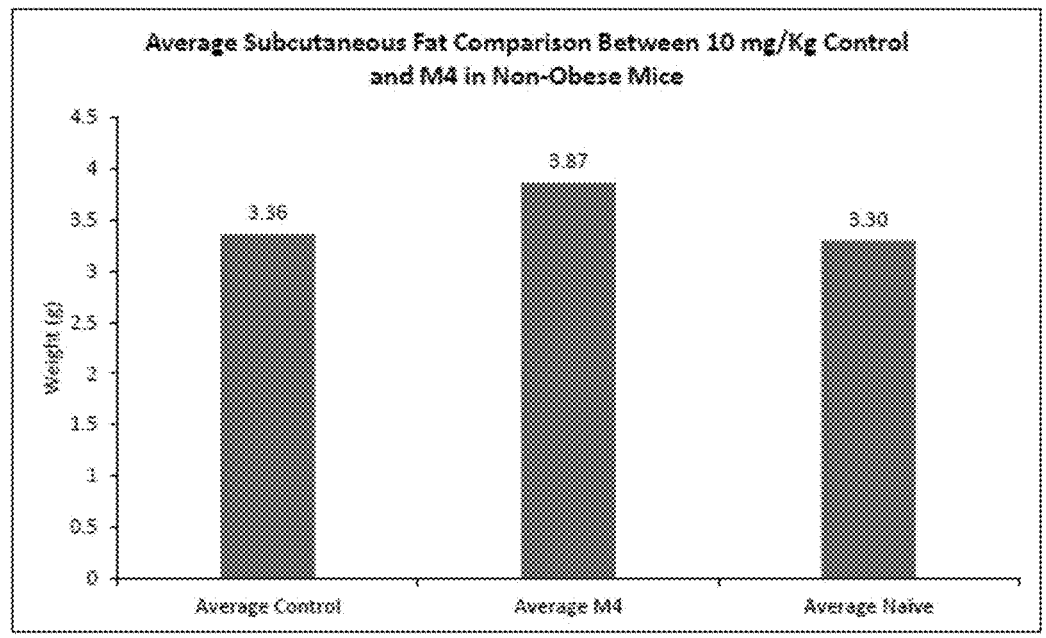
FIG. 20

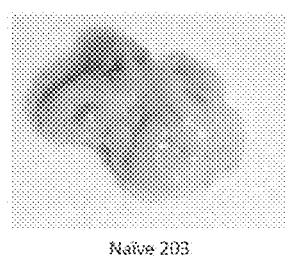 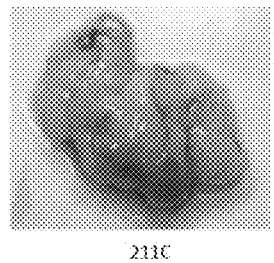 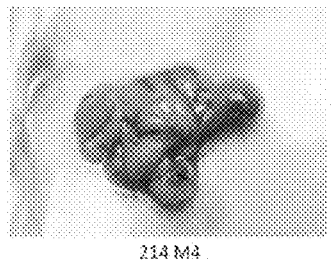
FIG. 21A          FIG. 21B          FIG. 21C
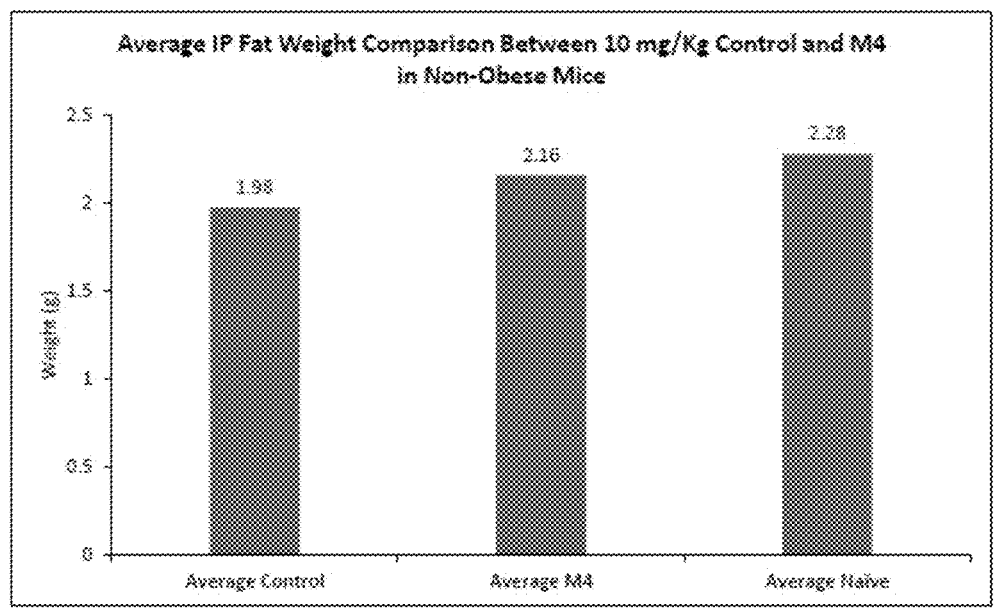
FIG. 22
 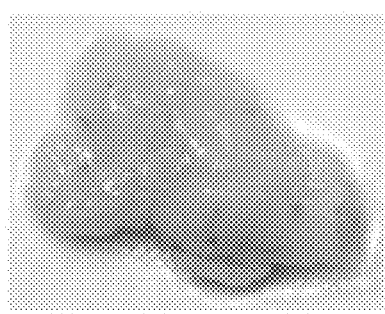 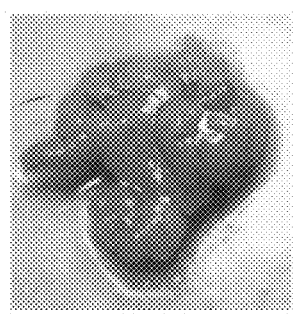
FIG. 23A          FIG. 23B          FIG. 23C

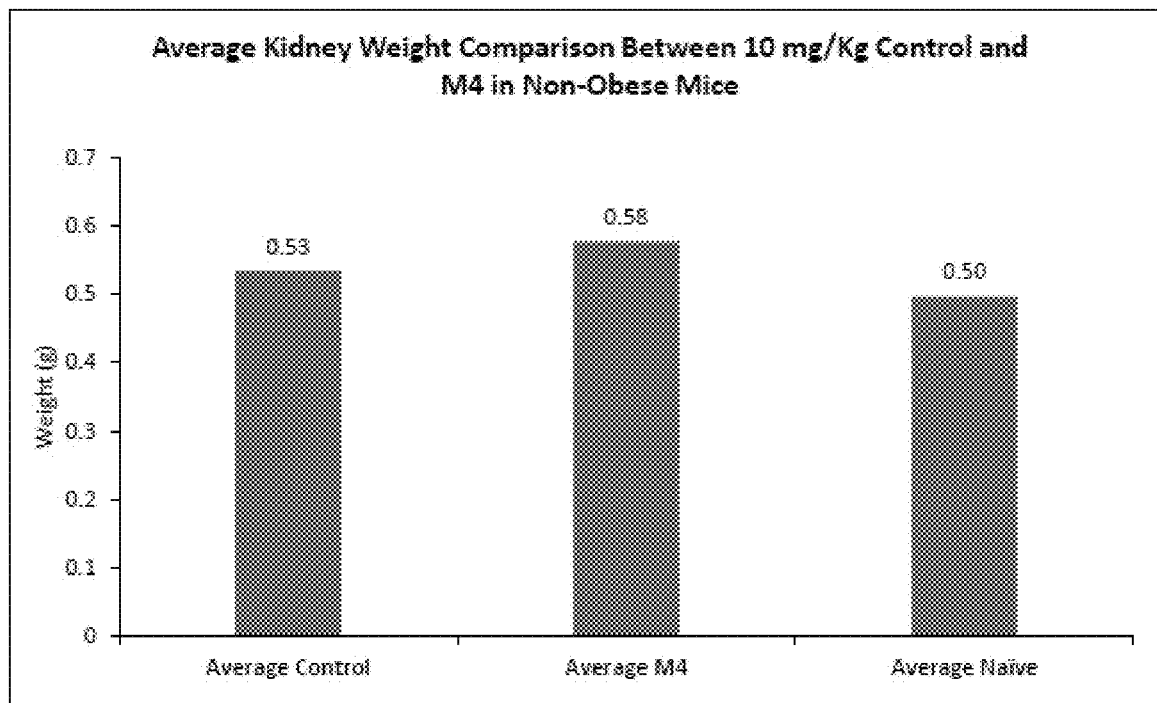
FIG. 24
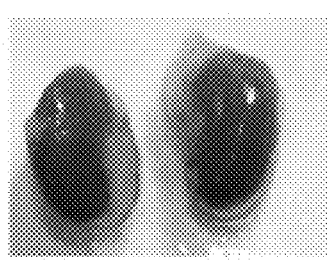 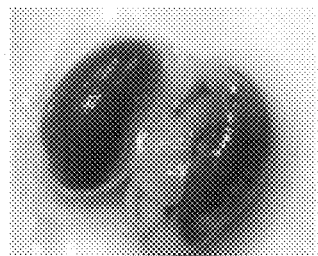 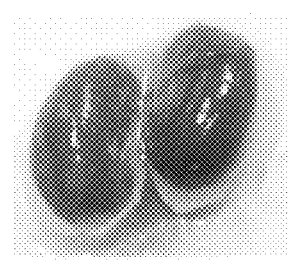
FIG. 25A     FIG. 25B     FIG. 25C

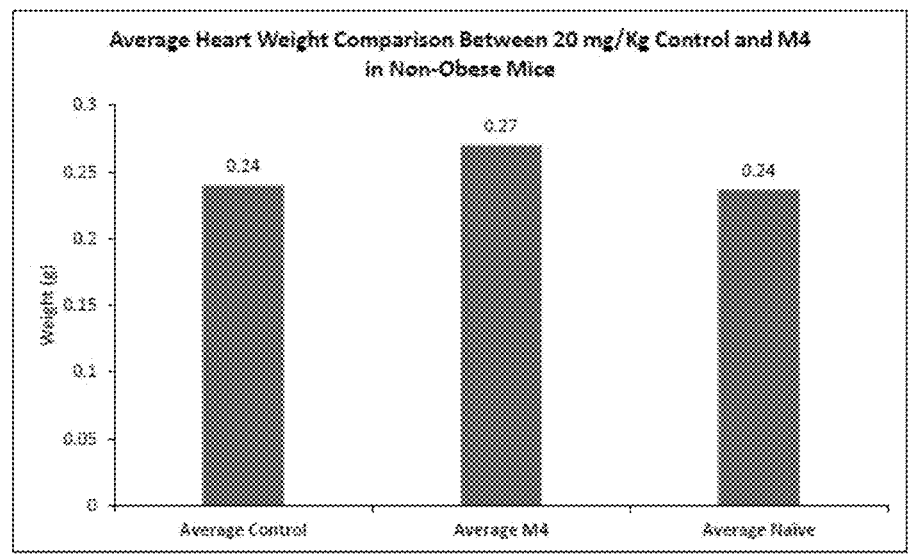
FIG. 31
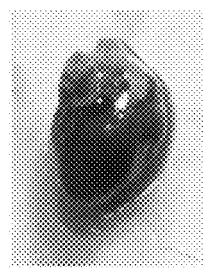 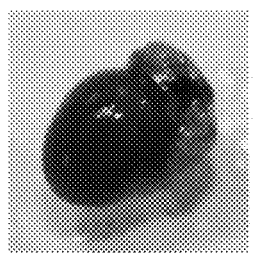 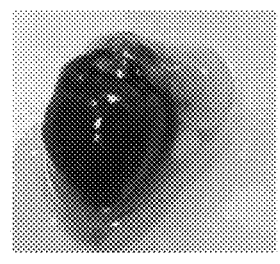
FIG. 32A   FIG. 32B   FIG. 32C
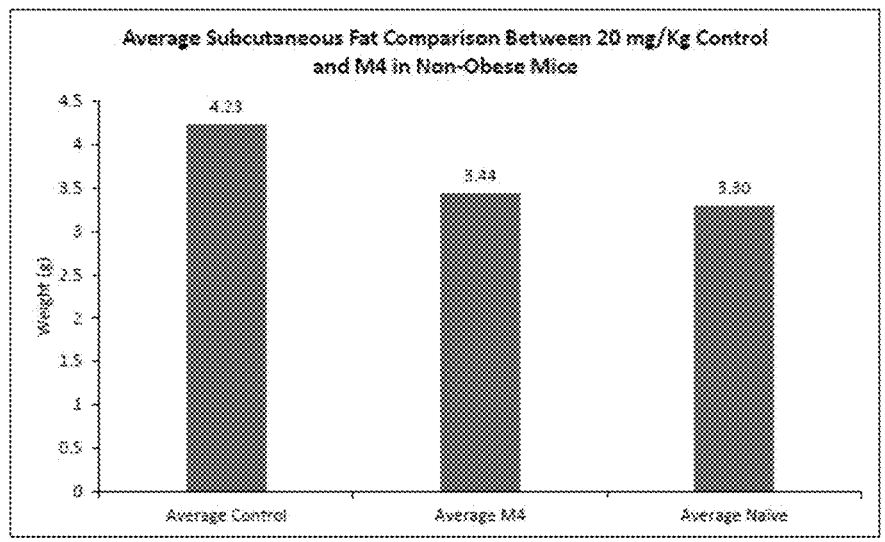
FIG. 33

Naïve 203
2.86 g

217 C
3.79 g

221 M4
4.33 g

Naïve 203
2.08 g

217 C
2.19 g

221 M4
3.06 g

 
FIG. 41A                FIG. 41B
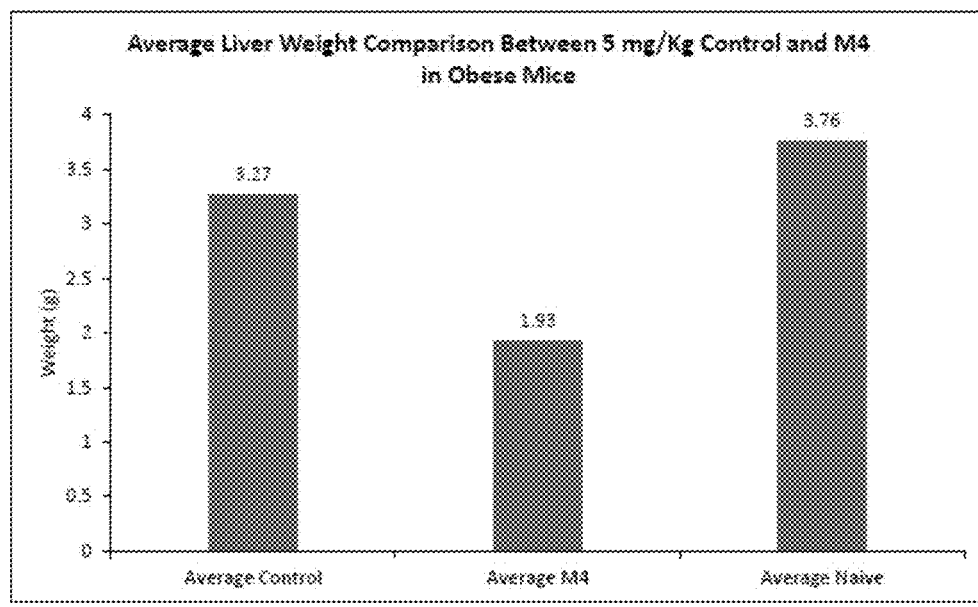
FIG. 42
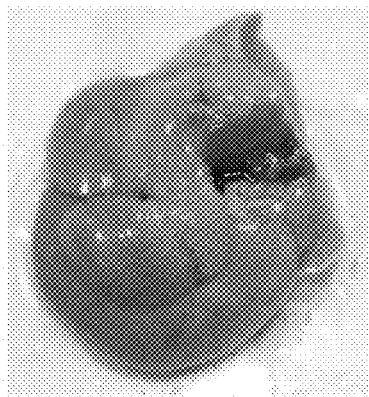 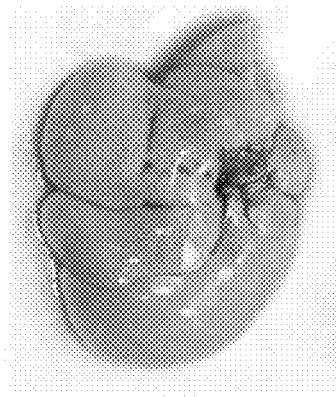 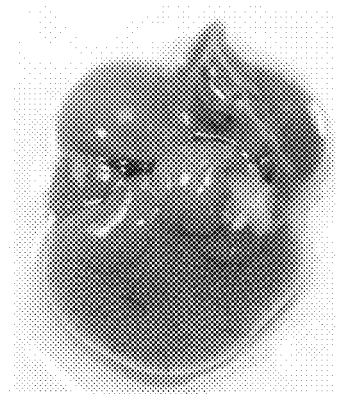
FIG. 43A                FIG. 43B                FIG. 43C

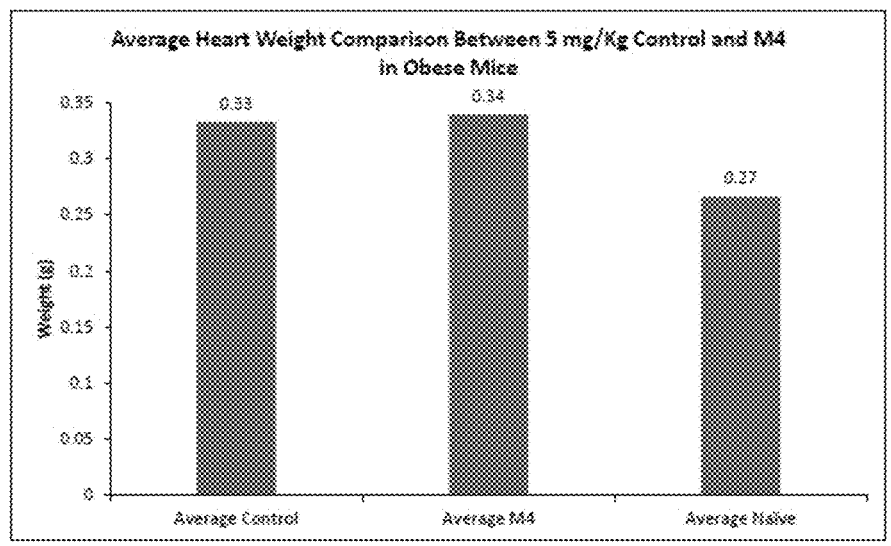
FIG. 44
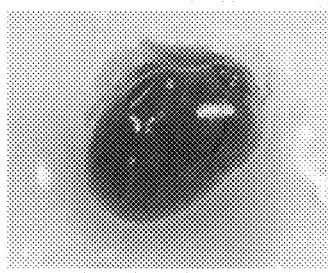
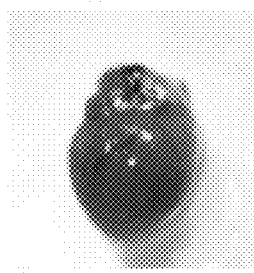
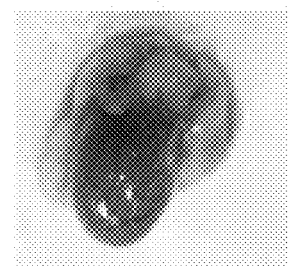
FIG. 45A      FIG. 45B      FIG. 45C
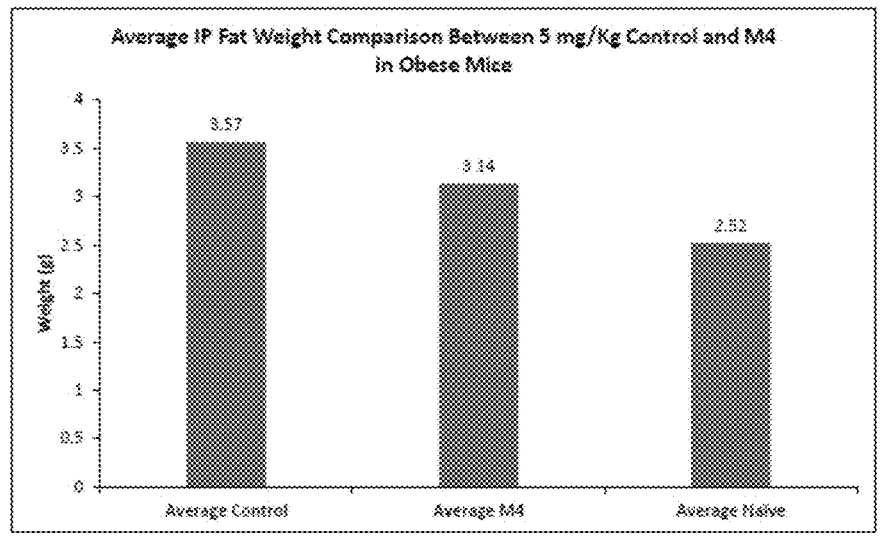
FIG. 46

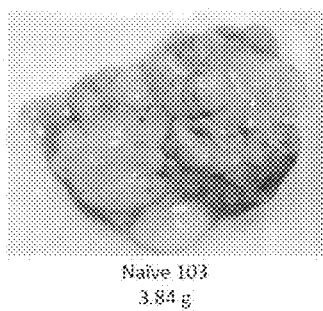
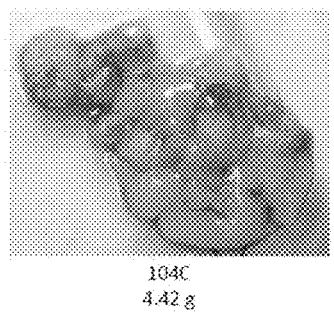
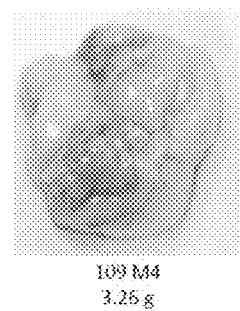
FIG. 47A      FIG. 47B      FIG. 47C
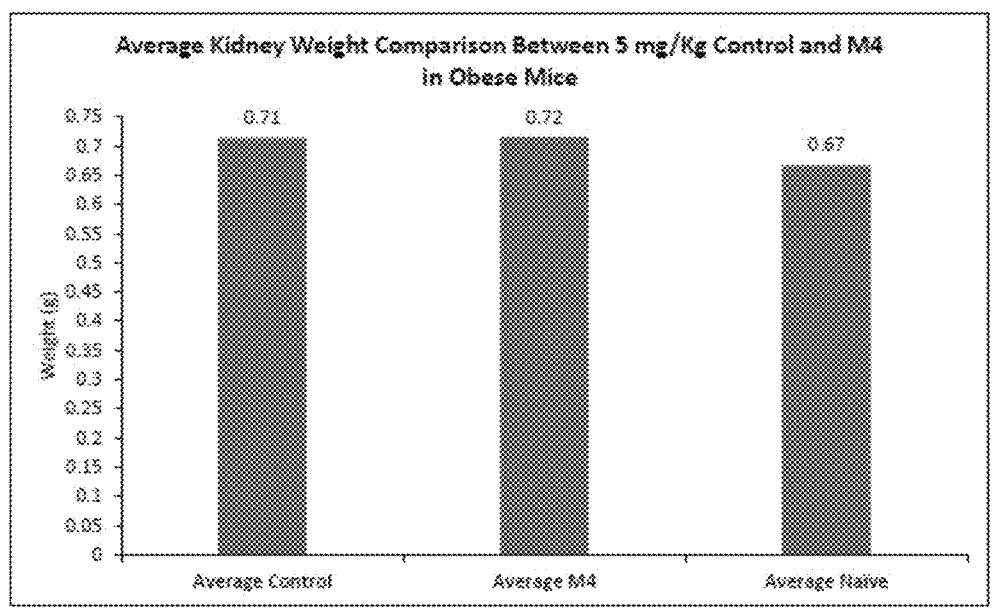
FIG. 48
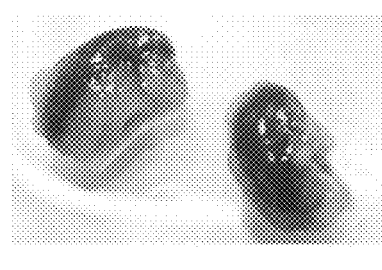
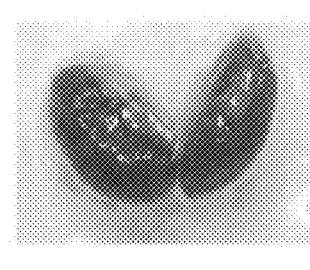
FIG. 49A      FIG. 49B      FIG. 49C

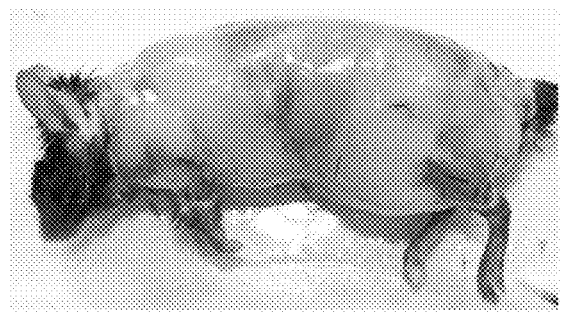
FIG. 52A
FIG. 52B
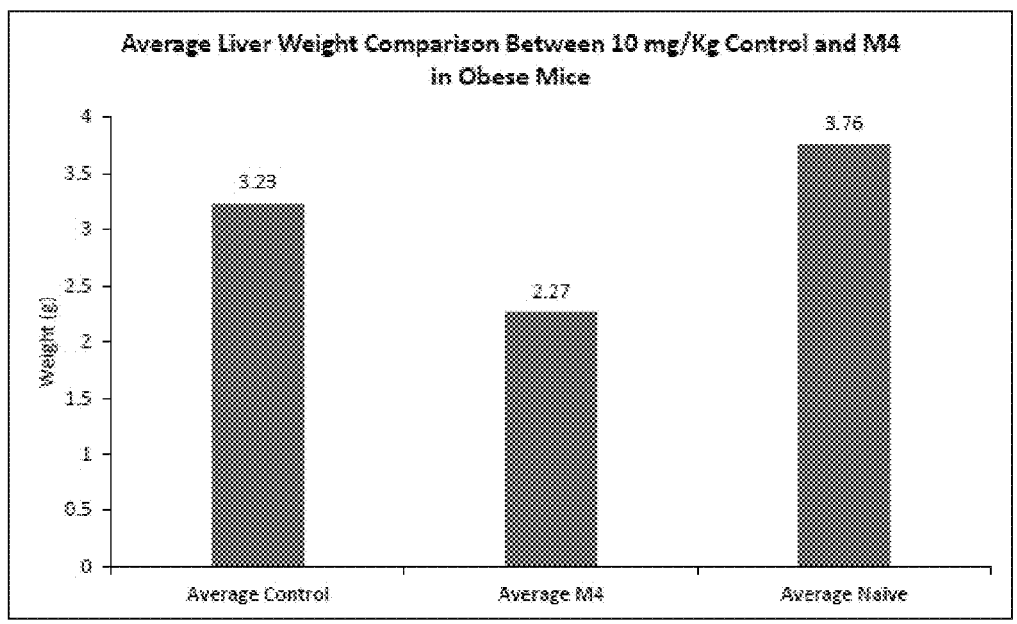
FIG. 53
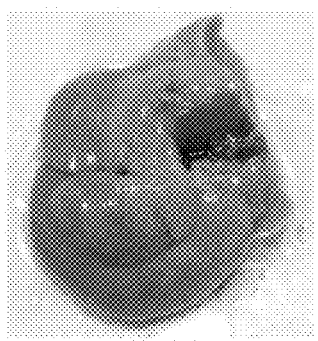
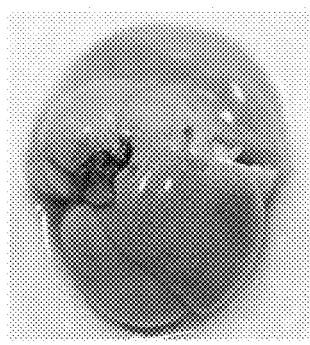
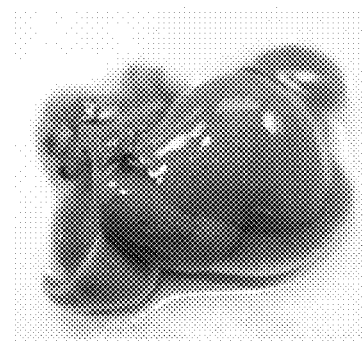
FIG. 54A
FIG. 54B
FIG. 54C Naive 103
0.29 g 112 C
0.48 g 115 M4
0.46 g

 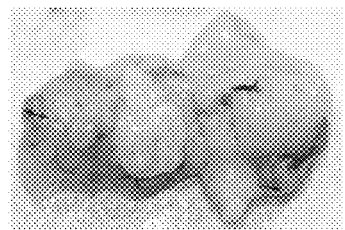 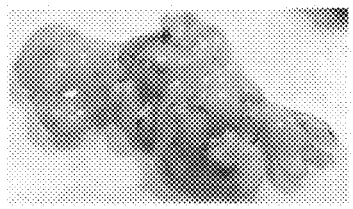
FIG. 58A      FIG. 58B      FIG. 58C
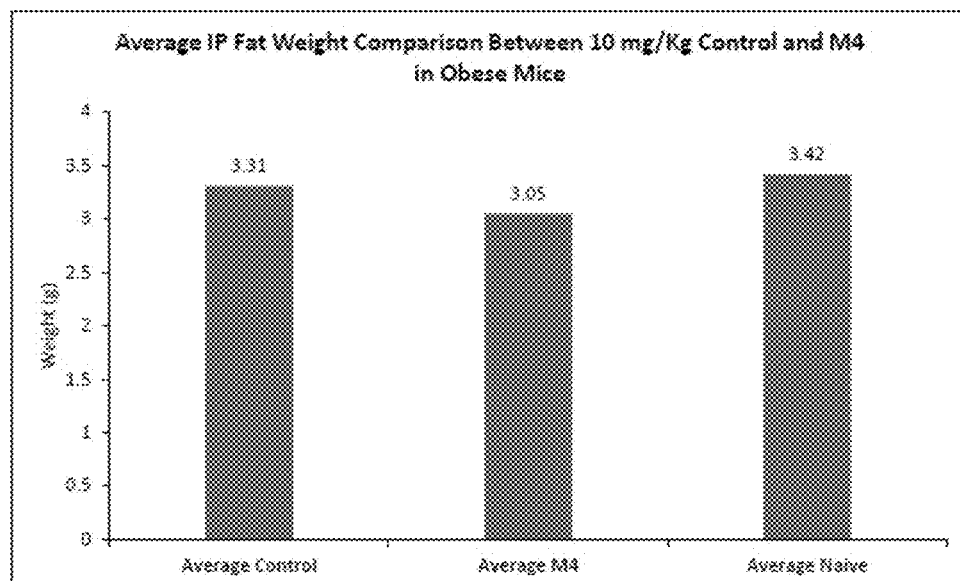
FIG. 59
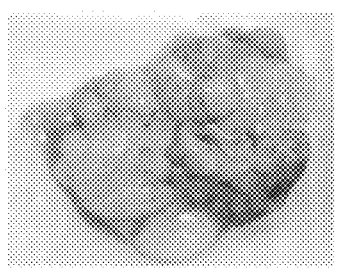 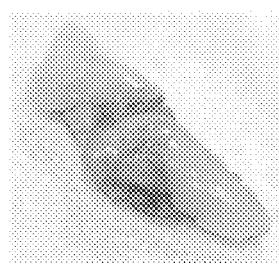 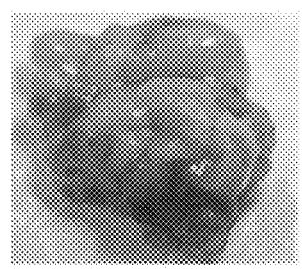
FIG. 60A      FIG. 60B      FIG. 60C

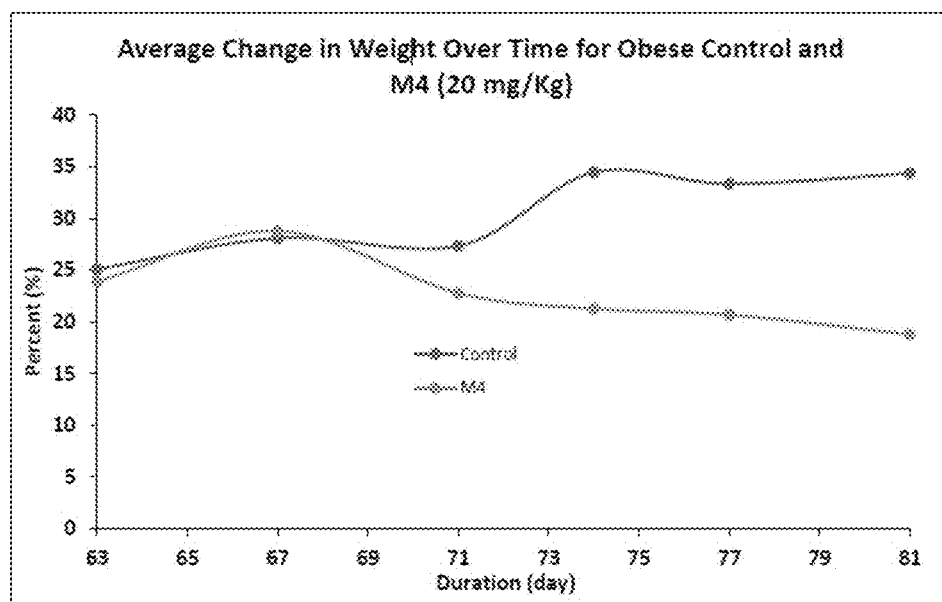
FIG. 64
  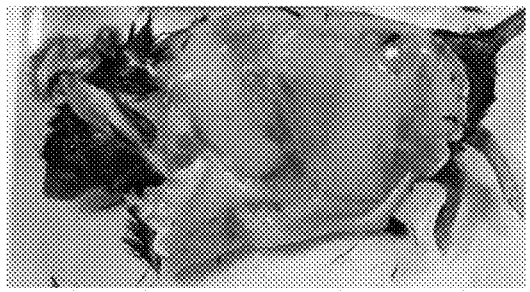
FIG. 65A  FIG. 65B
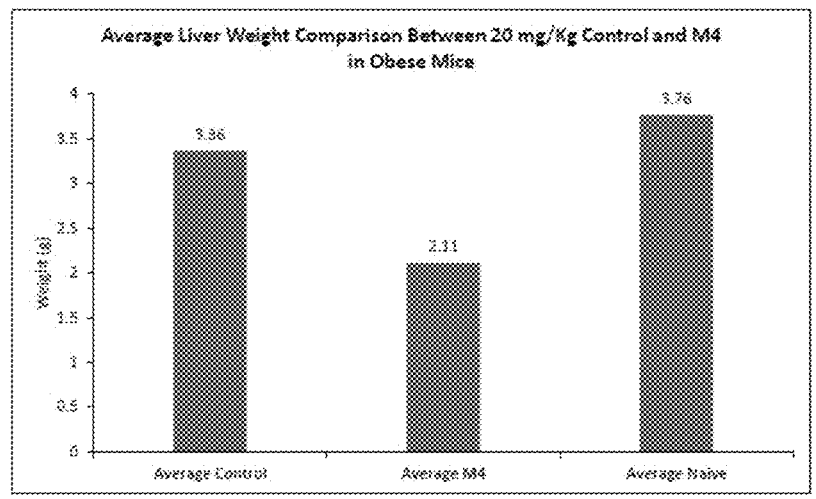
FIG. 66

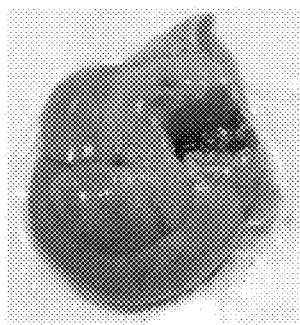
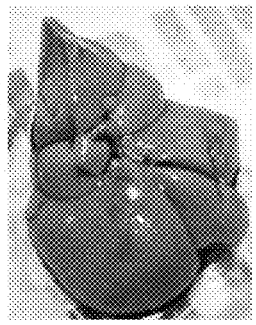
FIG. 67A     FIG. 67B     FIG. 67C
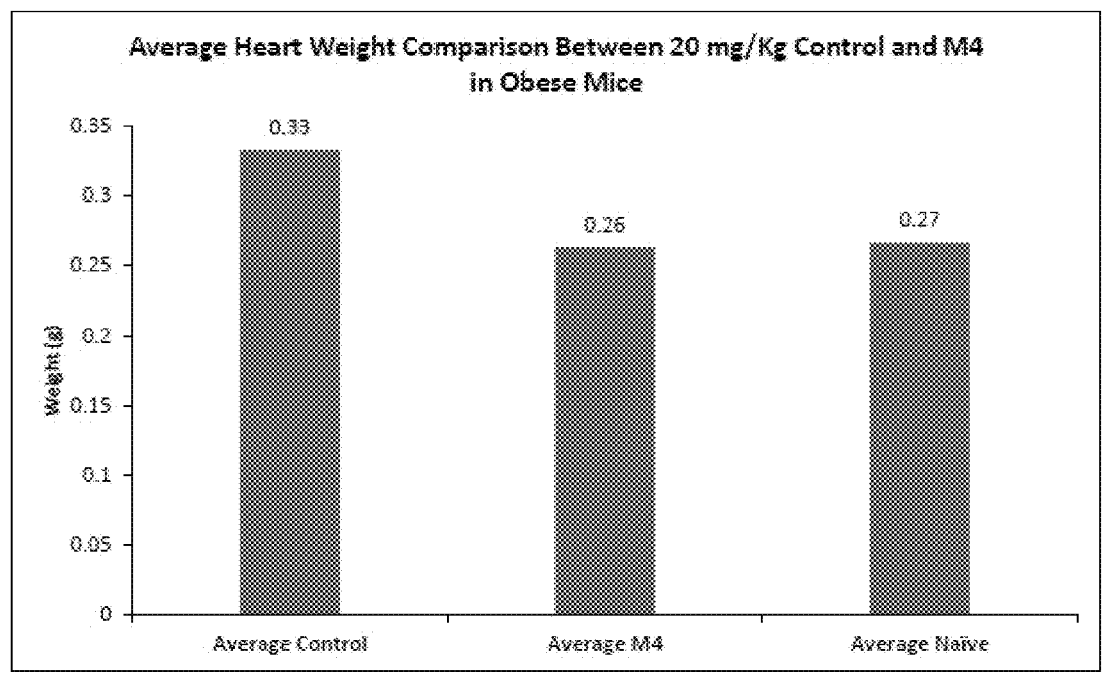
FIG. 68
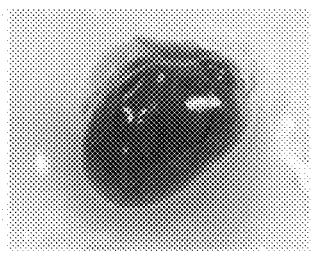
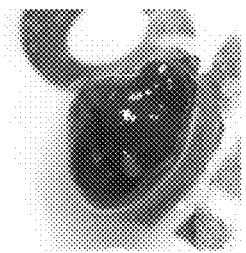
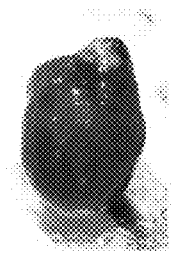
FIG. 69A     FIG. 69B     FIG. 69C

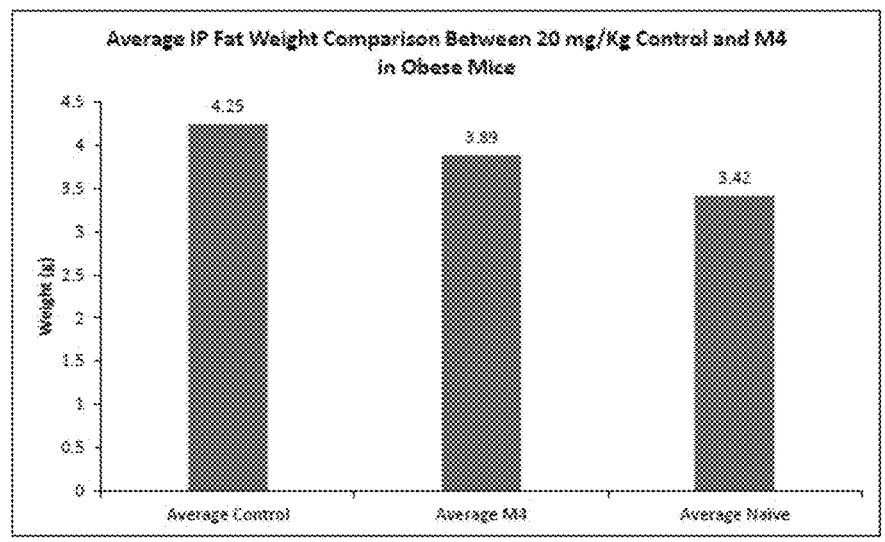
FIG. 70
 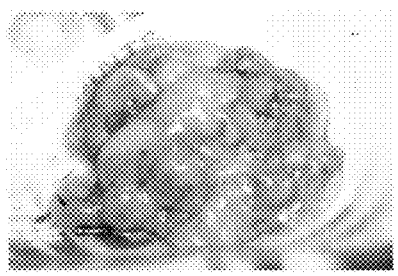 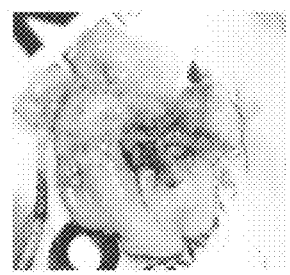
FIG. 71A        FIG. 71B        FIG. 71C
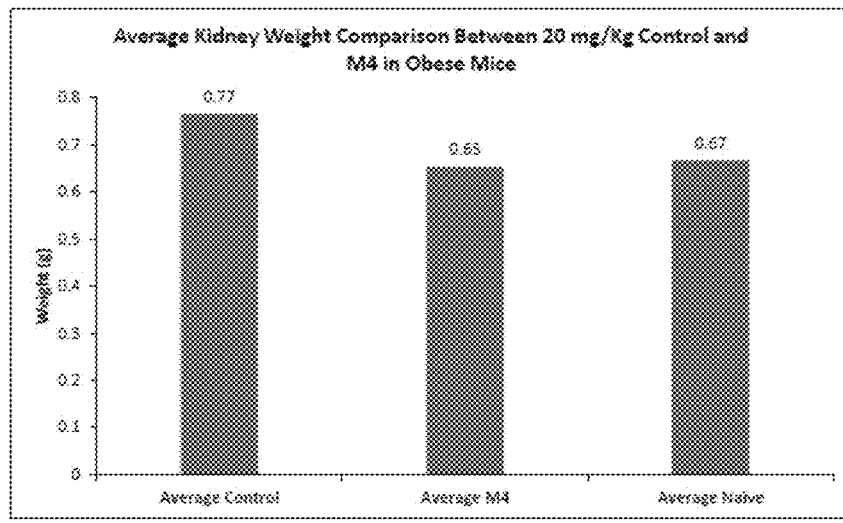
FIG. 72

Naïve 103
0.62 g 116C
0.80 g

119 M4
0.60 g

Lipid Engorged Adipocytes
N = 280

Lipid Engorged Adipocytes
N = 10

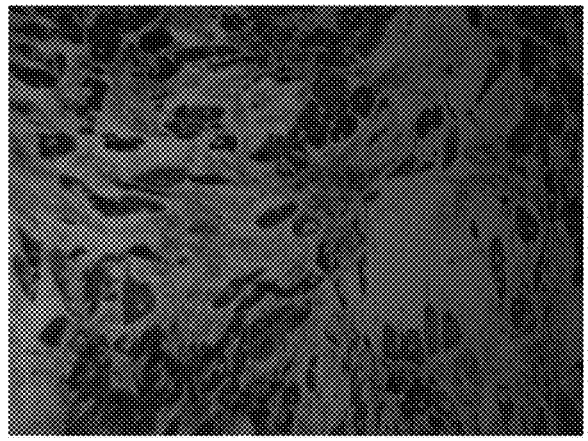
FIG. 79A  FIG. 79B
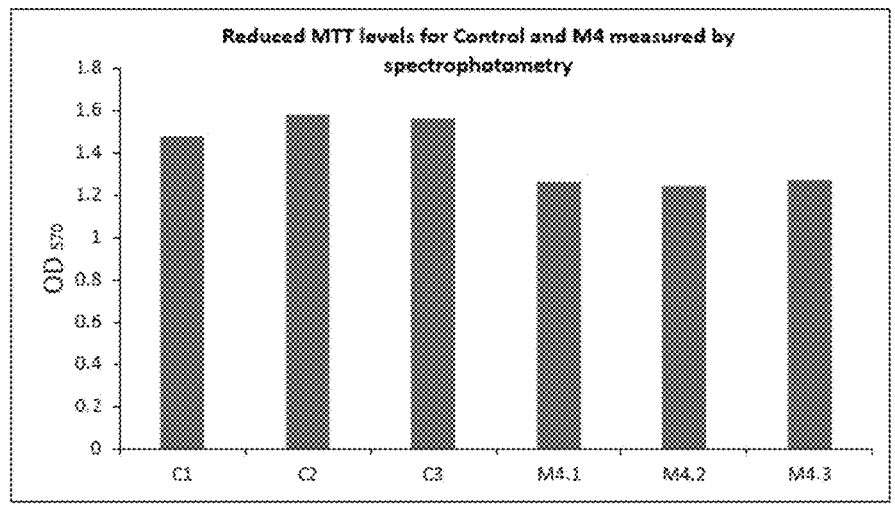
FIG. 80

METHODS AND FORMULATIONS FOR THE TREATMENT OF OBESITY AND OBESITY-RELATED METABOLIC DISEASES

REFERENCE MATERIALS

A sequence and/or variant listing is provided herein and attached in a separate sequence listing .txt file. The provided listings are incorporated herein by reference.

BACKGROUND OF THE INVENTION

The present invention relates to methods and formulations of treatment of metabolic diseases. The invention has particular utility in connection with treatment of obesity and in general, although treatment of other obesity-related metabolic related diseases and conditions including but not limited to diabetes, muscle loss due to deconditioning, Duchenne muscle dystrophy (DMD), nonalcoholic fatty liver disease or nonalcoholic steatohepatitis (NASH), cancer recovery, hypertension and/or dyslipidemia also advantageously may be treated.

Over 1.9 billion people globally are overweight and of those people, more than 650 million are obese. Obesity is the second leading cause of preventable death in the United States and a growing epidemic. Being obese significantly increases the risk of other diseases, such as cardiovascular disease, type II diabetes, endometrial cancer, liver cancer, kidney cancer, and pancreatic cancer. Currently, approximately 5% of all deaths in the United States are related to obesity.

Current treatments for obesity have limited results and serious side effects. For example, prescription medications that target the central nervous system, hormonal pathways, and/or gastrointestinal tract exhibit minimal physical improvement and carry significant side effects. Bariatric surgery, including gastric bypass, LAP-band, and gastric sleeve procedures are highly invasive and expensive. Lifestyle changes, such as diet and exercise, are not applicable for serious cases of obesity and exhibit mixed results.

The risk factors contributing to obesity are complex and diverse. In particular, genetic factors, medical conditions, energy intake, energy expenditure, socioeconomic factors, and/or psychosocial factors may all contribute to an individual's risk for obesity. Previously known treatments for obesity and related conditions are inadequate and typically only address one or two of these risk factors.

SUMMARY OF THE INVENTION

Therapeutic compounds and formulations for the treatment of obesity and obesity related metabolic diseases are described herein, along with methods of production and use. The disclosed therapeutic agents can significantly improve long-term obesity outcomes as compared to other treatment options currently available. To date, the disclosed therapies have been demonstrated to alter the biological characteristics of mice, human muscle cells, and adipocytes. These effects have been well documented in murine models, which lead to significant weight-loss and muscle gain in obese mice. As disclosed in detail below, the disclosed therapeutics and treatment methods are designed to promote muscle growth and also decrease adipocytes in patients (e.g., humans and other animals).

The disclosed therapeutic formulations are novel gene pathway regulators and work to provide initial treatment, promote growth and metabolic change, and provide long-lasting effects. Specifically, at the start of treatment, a cocktail formulation regulates the expression of several genes to increase the growth of skeletal muscle and diminish accumulation of fat in adipocytes. During treatment, growth and metabolic change occurs as skeletal muscle mass begins to increase by burning adipocyte mass and fat storage. As treatment continues, long-lasting effects are experienced (such as persistent diminished fat accumulation), even after therapeutic formulations are no longer provided to a patient.

In one aspect of the invention there is provided a method for treatment of obesity and obesity-related metabolic diseases in animals including humans which method comprises increasing the animal's metabolic function by administering to the animal a therapeutically effective amount of an antisense oligonucleotide.

In one embodiment the antisense oligonucleotide has a structure defined by the following formula:

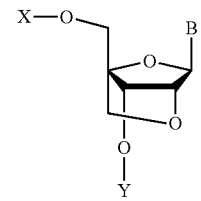

wherein B is a pyrimidine or purine nucleic acid base, an analogue thereof, X and Y are identical or different, and each represents a hydrogen atom, an alkyl group, an alkenyl group, an alkynyl group, a cycloalkyl group, an aralkyl group, an aryl group, an acyl group, or a silyl group, or an amidite derivative thereof. In such embodiment, B preferably includes the following sequence:

5'GTTGAGATAGCATCAG-3' (SEQ ID NO: 1).

In another embodiment the therapeutic agent may be administered orally, parenterally, topically, directly to the lungs, rectally or vaginally.

In one embodiment the antisense oligonucleotide is administered in a dose of between 1 mg/kg and 20 mg/kg based on the patient's weight in kg. In such embodiment, the dose preferably is administered once, twice or, three time or more per day.

In another embodiment treatment is continued daily for 30, 45, 60 or 90 days.

In another embodiment, the disease is selected from the group consisting of nonalcoholic fatty liver disease, metabolic syndrome, Duchenne muscular dystrophy (DMD), diabetes, cancer recovery, muscle loss due to deconditioning, hypertension, nonalcoholic steatohepatitis (NASH), dyslipidemia and obesity.

The present invention also provides a therapeutic formulation for treatment of obesity, and obesity-related metabolic diseases comprising an antisense oligonucleotide in a pharmaceutically acceptable carrier therefor.

In one embodiment, the antisense oligonucleotide has a structure defined by the following formula:

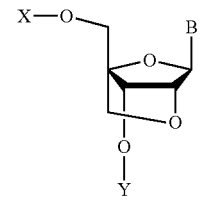

wherein B is a pyrimidine or purine nucleic acid base, an analogue thereof, X and Y are identical or different, and each represents a hydrogen atom, an alkyl group, an alkenyl group, an alkynyl group, a cycloalkyl group, an aralkyl group, an aryl group, an acyl group, or a silyl group, or an amidite derivative thereof. In such embodiment, B preferably includes the following sequence:

5'GTTGAGATAGCATCAG-3' (SEQ ID NO: 1).

In the working examples below, this compound is designated as "M4".

In another embodiment the therapeutic agent is in a pharmaceutically acceptable carrier selected form the group consisting of a tablet, capsule, liquid, solution, suspension, syrup, elixir, cream, ointment, lotion, gel, patch, dry powder and suppository.

In yet another embodiment, the antisense oligonucleotide is in an unit dosage form.

In still yet another embodiment, the disease is selected from the group consisting of nonalcoholic fatty liver disease, metabolic syndrome, Duchenne muscular dystrophy (DMD), diabetes, cancer recovery, muscle loss due to deconditioning, hypertension, nonalcoholic steatohepatitis (NASH), dyslipidemia and obesity.

DETAILED DESCRIPTION OF THE INVENTION

Obesity has a number of etiological pathways. One such pathway of interest is limited muscle mass. Diet, inactivity, and/or genetic predisposition can lead to reduced muscle mass, increasing the inability to burn excess calories and lead to adipocytes storing excess calories as fat. The present disclosure provides therapeutic agents which effectively can regulate muscle growth of obese patients, through gene knockdown therapy, and improve their overall metabolic function. Specifically, the disclosed compounds and formulations have been shown to regulate the expression of several genes to increase the growth of skeletal muscle and diminish the accumulation of fat in adipocytes. Additionally, skeletal muscle mass begins to increase during the treatments as adipocyte mass is reduced. The therapies disclosed herein have also been demonstrated to provide long-lasting results, even months after treatment has concluded, with diminished fat accumulation reported after treatment.

As described below in detail below, the disclosed therapeutic agents (e.g., compounds, mixtures, formulations, and/or cocktails) include one or more antisense oligonucleotides with a locked backbone. For example, in some embodiments, the antisense oligonucleotide(s) used in the disclosed therapies may be prepared according to the methods described in U.S. Pat. Nos. 6,268,490, 6,770,748 and RE44,779, which is incorporated herein by reference. In some particular embodiments, the antisense oligonucleotide has a structure defined by the following formula:

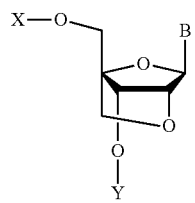

wherein B is a pyrimidine or purine nucleic acid base, an analogue thereof, X and Y are identical or different, and each represents a hydrogen atom, an alkyl group, an alkenyl group, an alkynyl group, a cycloalkyl group, an aralkyl group, an aryl group, an acyl group, or a silyl group, or an amidite derivative thereof.

The alkyl group represents a straight chain or branched chain alkyl group with 1 to 20 carbon atoms. Its examples include methyl, ethyl, n-propyl, i-propyl, n-butyl, t-butyl, pentyl, hexyl, heptyl, octyl, nonyl and decyl.

The alkenyl group represents a straight chain or branched chain alkenyl group with 2 to 20 carbon atoms. Its examples include vinyl, allyl, butenyl, pentenyl, geranyl, and farnesyl.

The alkinyl group represents a straight chain or branched chain alkinyl group with 2 to 20 carbon atoms. Its examples include ethynyl, propynyl, and butynyl.

The cycloalkyl group represents a cycloalkyl group with 3 to 8 carbon atoms, and includes, for example, cyclopropyl, cyclobutyl, cyclopentyl, cyclohexyl, cycloheptyl, and cyclooctyl. Another example is a heterocyclic group in which one or more arbitrary methylene groups on the ring of the cycloalkyl group have been substituted by an oxygen atom, a sulfur atom, or an alkyl-substituted nitrogen atom. It is, for instance, a tetrahydropyranyl group.

The aryl group refers to a monovalent substituent formed by removing one hydrogen atom from an aromatic heterocyclic group or an aromatic hydrocarbon group. Preferably, it represents a monovalent substituent formed by removing one hydrogen atom from an aromatic hydrocarbon group, and includes, for example, phenyl, tolyl, xylyl, biphenyl, naphthyl, anthryl, and phenanthryl. The carbon atom on the ring of the aryl group may be substituted by one or more of a halogen atom, a lower alkyl group, a hydroxyl group, an alkoxyl group, an amino group, a nitro group, and a trifluoromethyl group. The substituent in this case is, for example, a halogen atom, a hydroxyl group, an amino group, an alkoxy group, or an aryloxy group.

The aralkyl group refers to an alkyl group bonded to an aryl group, and may be substituted. The aralkyl group that may be substituted represents an alkyl group bonded to an aryl group, with one or more arbitrary hydrogen atoms of the aryl group and the alkyl group being optionally substituted by the following substituents: Examples of the substituents are acyl, amino, aryl, alkyl, cycloalkyl, alkoxy, hydroxyl, nitro, and halogen.

The amino group need not be substituted, but the amino group when substituted includes, for example, alkylamino, arylamino, and acylamino. Examples of the alkoxy group are methoxy, ethoxy, n-propoxy, 1-propoxy, n-butoxy, 1-butoxy, s-butoxy, t-butoxy, pentyloxy, hexyloxy, and phenoxy. Examples of the halogen atom are fluorine, chlorine, bromine, and iodine.

The preferred examples of the aralkyl group are trityl, benzyl, phenethyl, tritylmethyl, diphenylmethyl, naphthylmethyl, and 4,4'-dimethoxytrityl (DMTr). Particularly preferred is a DMTr group.

As the acyl group, acetyl, formyl, propionyl, benzoyl, and benzyloxycarbonyl can be exemplified. An example of the silyl group is a trialkylsilyl group, preferably trimethylsilyl, triethylsilyl, triisopropylsilyl, t-butyldimethylsilyl or t-butyldiphenylsilyl, and more preferably trimethylsilyl.

In select embodiments, B includes the following sequence:

5'GTTGAGATAGCATCAG-3' (SEQ ID NO: 1).

which we designated as "M4".

The antisense oligonucleotide(s) and other therapeutic compounds (if present) may be administered to a patient in liquid or solid form. In some embodiments, the therapeutic agents may be administered orally (e.g., as a tablet, capsule, liquid, solution, suspension, syrup, or elixir), parenterally (e.g., through a needle or catheter inserted intravenously, intramuscularly, subcutaneously, intra-arterial, intrathecally, or intradermally), topically (e.g., as a cream, ointment, lotion, gel, or transdermal patch), rectally or vaginally (e.g., as a suppository) or directly to the lungs (e.g., using a DPI, MDI or nebulizer).

The therapeutic compounds may be administered to a patient using any dosing scheme determined appropriate by a medical professional. In some example embodiments, a dose of between 1 mg/Kg and 20 mg/Kg may be administered to a patient (based on the patient's weight in Kg). In other embodiments, however, dosing may be 2, 4, 6, 8, 10, 12, 14, 16 or 18 mg/Kg (based on the patient's weight in Kg.)

In some embodiments, a patient may be treated with an appropriate dose of therapeutic agent once, twice, three times, or more during a day. Treatment may continue for a select number of days, such as 30 days, at 45 days, at 60 days, at 90 days, or more.

After treatment has concluded, the patient may exhibit measurable improvements in physical health. For example, in some cases, patients may experience increased muscle mass, a reduction in fat cells, and/or other improvements during or after treatment. In some particular embodiments, a patient may experience at least 5%, 10%, 15%, 20%, 25%, 30%, 35%, 40%, or more fat loss (after, for example 30 days of treatment). In these and other embodiments, a patient may exhibit a gain in muscle of at least 5%, 10%, 15%, 20%, 25%, 30%, 35%, or more (after, for example 30 days weeks of treatment). Numerous other health improvements may also be experienced by a patient during and after treatment.

The patent or application file contains at least one drawing executed in color. Copies of this patent or patent application publication with color drawing(s) will be provided by the Office upon request and payment of the necessary fee.

In some embodiments, health improvements experienced during treatment may persist after treatment. For example, in some embodiments, muscle gain and/or fat loss experienced during treatment may continue or stabilize after treatment for a period of at least three months, at least six months, at least nine months, or more.

In addition to treating obesity, the disclosed formulations also may be used to treat, prevent, and/or manage symptoms of other obesity-related metabolic diseases and conditions, such as nonalcoholic fatty liver disease, metabolic syndrome, Duchenne muscular dystrophy (DMD), diabetes, muscle loss due to deconditioning cancer recovery, hypertension, nonalcoholic steatohepatitis (NASH) and/or dyslipidemia. During treatment, muscle cells grow at the expense of liver fat storage, thus reversing the cause of fatty liver. Metabolic improvements generated by treatment may also prevent the liver from accumulating excess fat after treatment. Metabolic syndrome includes several common symptoms, including high blood sugar (type-II diabetes), high blood pressure (hypertension), abnormal lipid counts (dyslipidemia), and a variety of other conditions. While current medicines for metabolic syndrome can only target these conditions individually, the disclosed treatments are capable of improving the whole metabolic system, thus treating the root causes of these diseases. DMD is a severe type of muscular dystrophy, and one of the most common X-linked recessive Mendelian diseases. Approximately 1 in 5,000 males are born with DMD, resulting in muscle loss, fat content increase and loss of the ability to walk. Currently, steroids (with extensive side effects) are the only available treatment for DMD. Compared to steroids, the disclosed treatments have higher efficacy and reduced side effects and thus have the potential to significantly improve the lives of DMD patients.

The disclosed therapeutic compounds and treatment methods are designed to reduce (and in some cases eliminate) obesity in a patient as well as related diseases and conditions. The disclosed compounds and methods may be used in any mammalian patient, including humans, primates, dogs, cats, mice, or any other mammal. Prior to conducting clinical trials in humans, experiments were conducted in mice and human adipocytes and myocytes. Clinical data from these trials are described below.

Murine Models

In a first clinical experiment, the effect of a therapeutic compound, as described above, at times referred to herein as "M4," was evaluated in obese and non-obese mice against a control.

The "M4" therapeutic compound administered to the test subjects was prepared following the teachings of U.S. Pat. No. RE44,779.

A total of 42 test subjects were included in the study, with 21 obese and 21 non-obese test subjects. The test subjects were provided with three different doses (5 mg/Kg, 10 mg/Kg and 20 mg/Kg) of the therapeutic compound for a period of four weeks. During the course of treatment, obese subjects were fed a 60% fat diet and non-obese subjects were fed a 10% fat diet. Weight of the test subjects was recorded twice a week.

The test subjects (mice) participating in the study were black 6 (B6-M) and diet-induced obese B6 (B6-DIO-M), provided by Taconic Biosciences. Both models shared the same genotype. Phenotypic differences in the test subjects were due to percent fat in diet (i.e., 10% as compared to 60%).

The diet for the test subjects was a rodent diet with 10% kcal % fat (#D12450J) and rodent diet with 60% kcal % fat (#D12492i), provided by Research Diets. Inc.

All test subjects were housed separately in a 0.22 micron high-energy particular absorber (HEPA) filtered vivarium. There were three treatment groups in the study: a low dose treatment group (5 mg/Kg), a medium dose treatment group (10 mg/Kg), and a high dose treatment group (20 mg/Kg). Three mice were included in each treatment group. Drug formulations and control formulations were administered via tail vein injection twice a week.

Three stock solutions of M4 and scrambled LNA were produced for the study and sterilized by filtration. The stock solutions were produced as follows: a 2.5 mg/mL for the 5 mg/Kg group, a 5 mg/mL solution for the 10 mg/Kg group, and a 10 mg/mL solution for the 20 mg/Kg group. For each treatment, a dosing of 2 µl/g was administered to the test subject. Dosing was determined by model weight (in grams).

BRIEF DESCRIPTION OF THE DRAWINGS

Non-Obese Low Dose Study Results

As shown in FIG. 1, the non-obese control exhibited a gradual increasing trend throughout the testing period and the group treated with M4 displayed a similar trend, however, weight change decreased after day 28 for the M4 group. Without wishing to be bound by theory, M4 seems to present higher weight gain as compared to the control. The weight gain observed is largely attributed to muscle gain in the individuals that have little fat to lose. At the end of the treatment time period, non-obese models who were injected with 5 mg/Kg of the control had 4.85% larger change in weight compared to those treated with M4.

As shown in FIG. 2, the non-obese control group exhibited a gradual increasing trend through the testing period and the M4 group displayed a slight increase, but exhibited fluctuations in weight change throughout days 59-85.

FIG. 5A shows the liver of a naïve mouse, FIG. 5B shows the liver of a control mouse, and FIG. 5C shows the liver of a mouse treated with M4.

FIG. 6 is a chart illustrating average heart weight for non-obese study participants who received a low dose (5 mg/Kg) treatment. As shown in FIG. 6, on average, non-obese control mice had the heaviest hearts while the naïve had the lightest hearts. However, the averages between the three groups are within the same range.

FIGS. 7A-7C are photographs showing the hearts of low dose study participants. In particular, FIG. 7A shows the heart of a naïve mouse, FIG. 7B shows the heart of a control mouse, and FIG. 7C shows the heart of a mouse treated with M4.

FIGS. 8A-8C are photographs showing subcutaneous fat of non-obese low dose (5 mg/Kg) study participants. In particular, FIG. 8A shows subcutaneous fat of a naïve specimen, FIG. 8B shows subcutaneous fat of a control specimen, and FIG. 8C shows subcutaneous fat of an M4 specimen.

FIG. 9 is a chart showing average IP fat for non-obese low dose (5 mg/Kg) study participants.

FIGS. 10A-10C are photographs showing IP fat of non-obese low dose (5 mg/Kg) study participants. In particular, FIG. 10A shows IP fat of a naïve specimen, FIG. 10B shows IP fat of a control specimen, and FIG. 10C shows IP fat of an M4 specimen.

FIG. 11A shows a kidney of a naïve specimen, FIG. 11B shows a kidney of a control specimen, and FIG. 11C shows a kidney of an M4 specimen.

No-Obese Medium Dose Study Results

Figure 1:
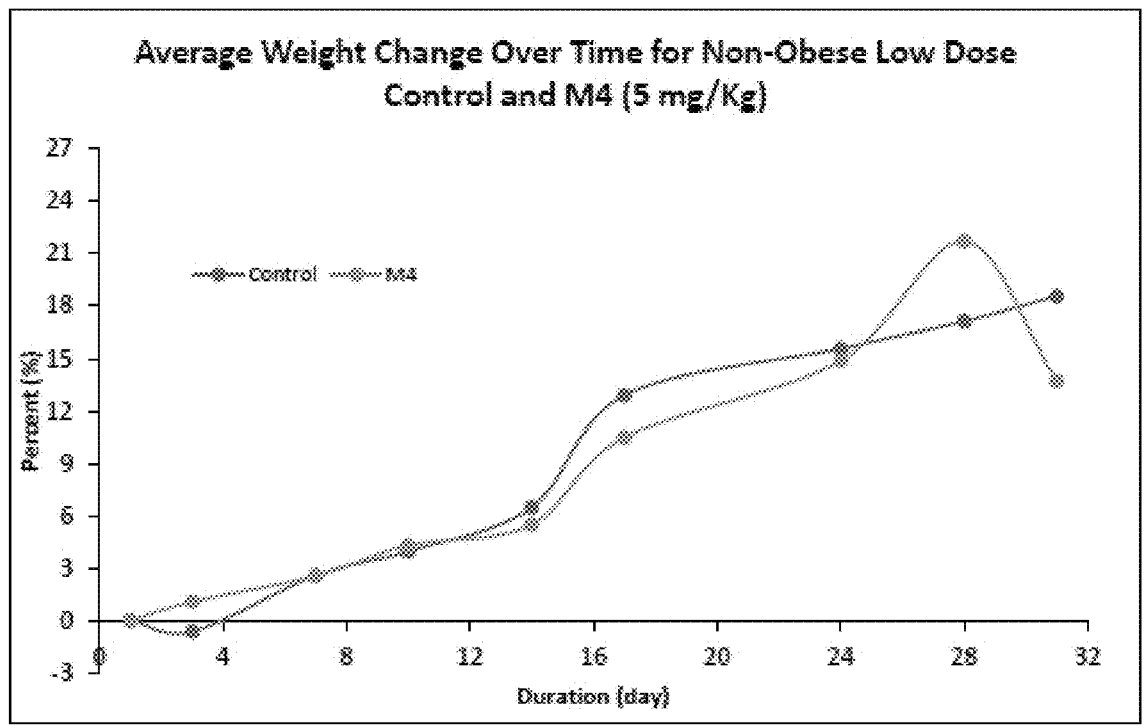
FIG. 1 illustrates the average weight change over time for the non-obese low dose (5 mg/Kg) control group and test group during days 1-32 of the study.
Figure 2:
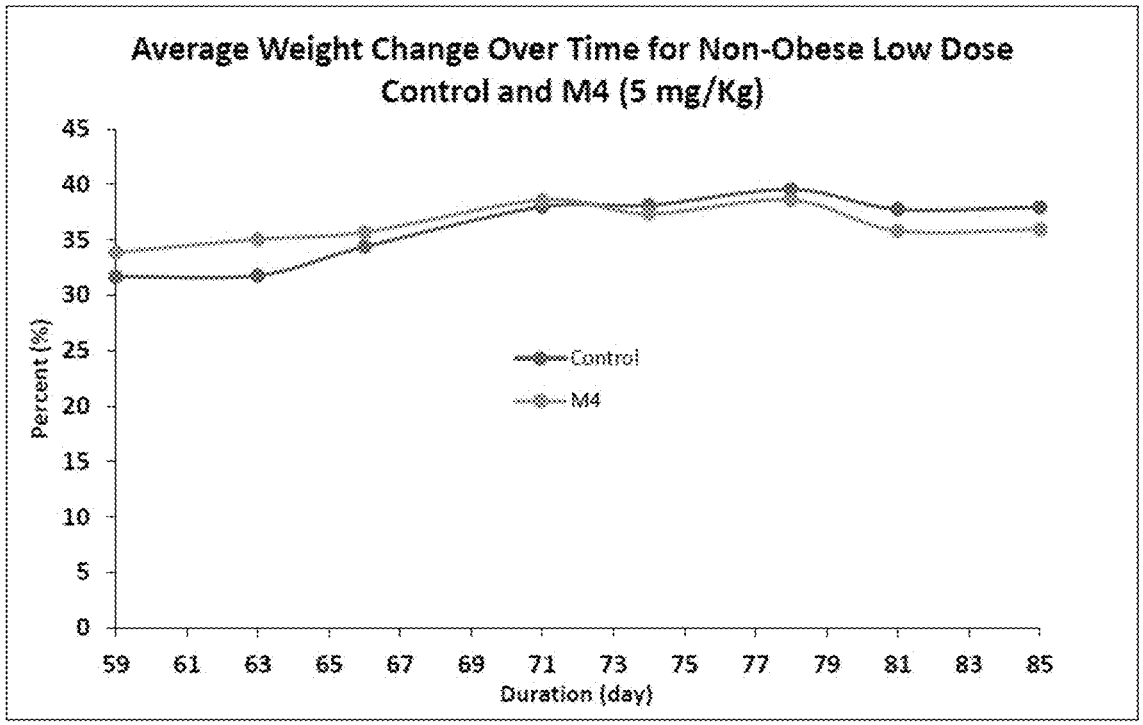
FIG. 2 illustrates the average weight change over time for the non-obese low dose (5 mg/Kg) control group and the group treated with M4 during days 59-85 of the study.
Figure 3A:
FIGS. 3A and 3B are photographs of the subcutaneous fat of non-obese test and control participants given the low dose (5 mg/Kg) treatment in the study.
Figure 3B:
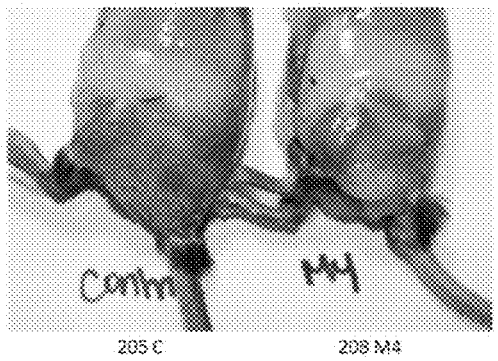
Figure 4A:
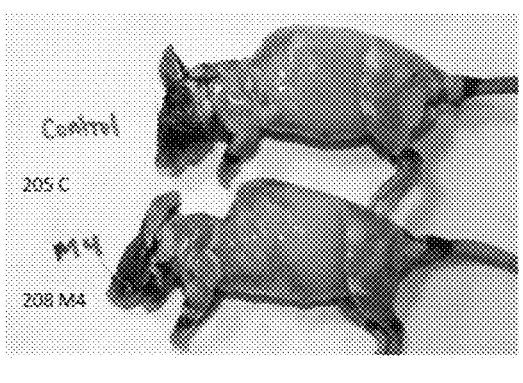
FIGS. 4A and 4B are photographs of the muscle (with subcutaneous fat removed) of non-obese test and control participants given the low dose (5 mg/Kg) treatment in the study.
Figure 4B:
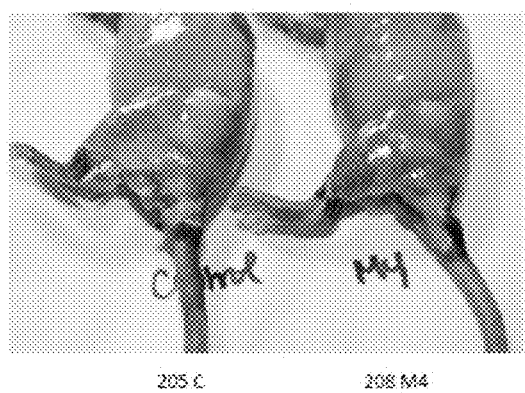
Figures 5A, 5B, 5C:
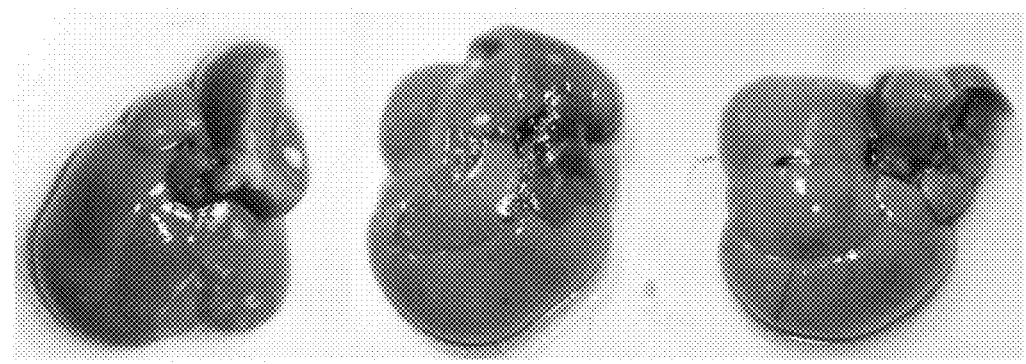
FIGS. 5A-5C are photographs of the livers of non-obese low dose study participants. In particular.
Figure 11A:
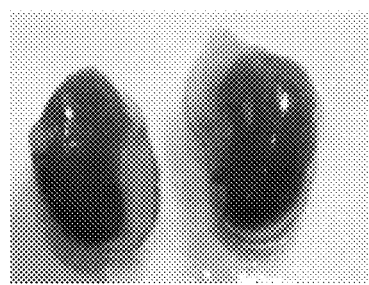
FIGS. 11A-11C are photographs showing kidneys of non-obese low dose (5 mg/Kg) study participants. In particular.
Figure 11B:
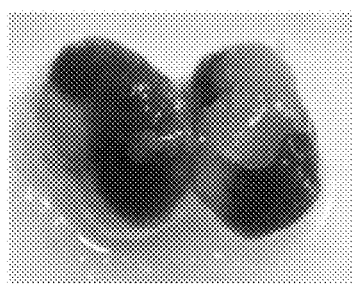
Figure 11C:
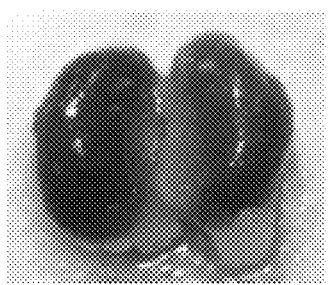
Figure 12:
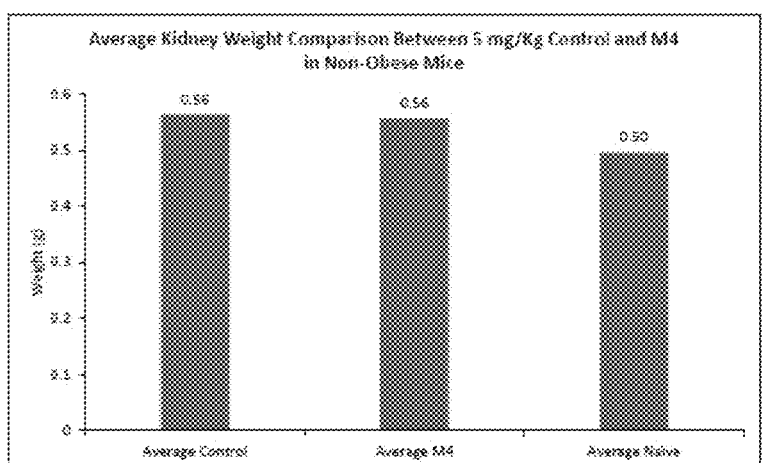
FIG. 12 is a chart of average kidney weight in non-obese low dose (5 mg/Kg) study participants.
Figure 13:
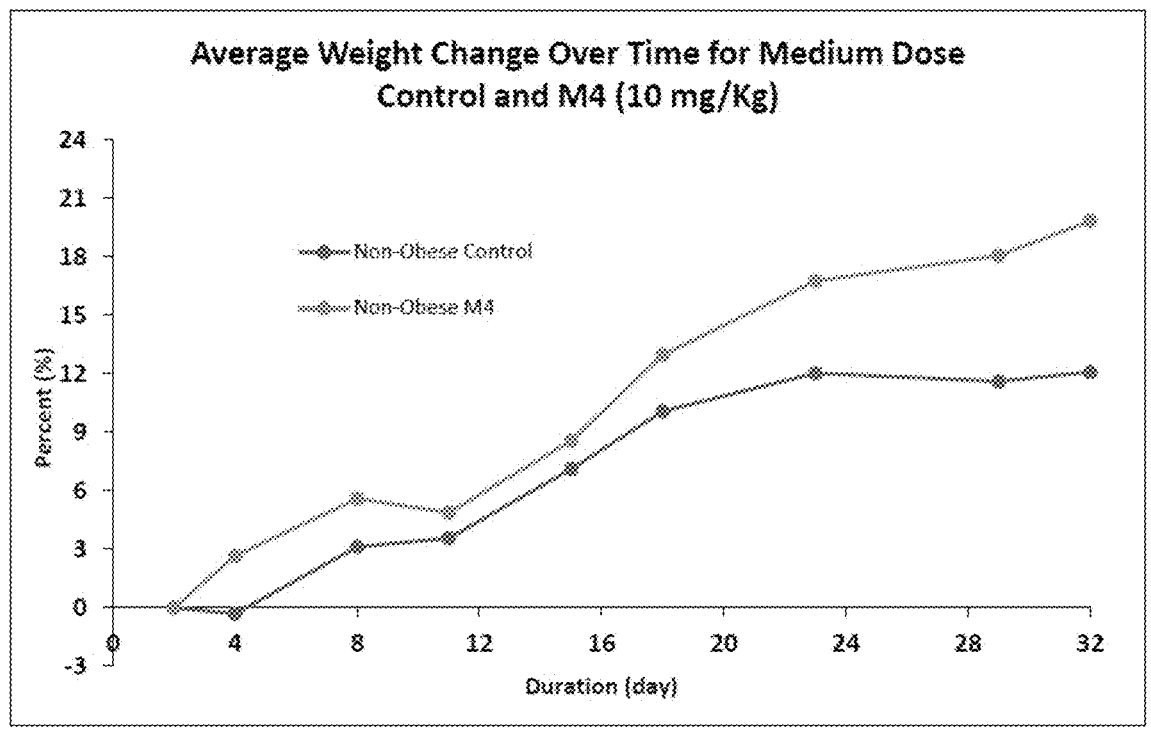

FIG. 13 illustrates the average weight change over time for the non-obese medium dose (10 mg/Kg) control group and test group during days 1-32 of the study. As shown in FIG. 13, both the control group and the group treated with M4 exhibited a positive weight change from day 2-32. Overall, M4 has the higher weight change pattern and specimens injected with M4 exhibited higher weight gain. At the end of the treatment period, non-obese participants injected with control had 7.73% smaller change in weight as compared to those injected with M4.

Figure 14:
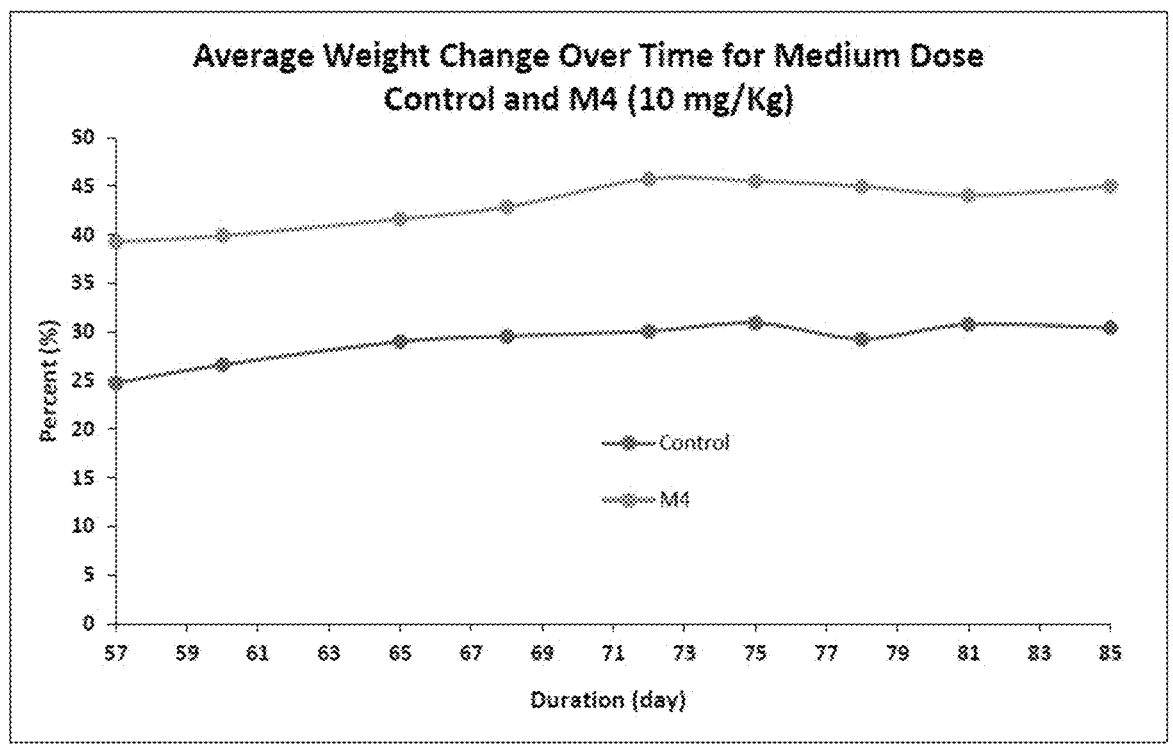

FIG. 14 illustrates the average weight change of these study participants during days 57-85 of the study.

FIGS. 15A and 15B are photographs of the subcutaneous fat of non-obese test and control participants given the medium dose (10 mg/Kg) treatment in the study.

FIGS. 16A and 16B are photographs of the muscle (with subcutaneous fat removed) of non-obese test and control participants given the medium dose (10 mg/Kg) treatment in the study.

FIG. 17 is a chart showing average liver weight for non-obese medium dose (10 mg/Kg) study participants.

FIGS. 18A-18C are photographs of the livers of non-obese medium dose study participants. In particular, FIG. 18A shows the liver of a naïve mouse, FIG. 18B shows the liver of a control mouse, and FIG. 18C shows the liver of a mouse treated with M4.

FIGS. 19A-19C are photographs showing the hearts of medium dose study participants. In particular, FIG. 19A shows the heart of a naïve mouse, FIG. 19B shows the heart of a control mouse, and FIG. 19C shows the heart of a mouse treated with M4.

FIG. 20 is a chart illustrating average subcutaneous fat for non-obese medium dose (10 mg/Kg) study participants.

FIGS. 21A-21C are photographs showing subcutaneous fat of non-obese medium dose (10 mg/Kg) study participants. In particular, FIG. 21A shows subcutaneous fat of a naïve specimen, FIG. 21B shows subcutaneous fat of a control specimen, and FIG. 21C shows subcutaneous fat of an M4 specimen.

FIG. 22 is a chart showing average IP fat for non-obese medium dose (10 mg/Kg) study participants.

FIGS. 23A-23C are photographs showing IP fat of non-obese medium dose (10 mg/Kg) study participants. In particular, FIG. 23A shows IP fat of a naïve specimen, FIG. 23B shows IP fat of a control specimen, and FIG. 23C shows IP fat of an M4 specimen.

FIG. 24 is a chart of average kidney weight in non-obese medium dose (10 mg/Kg) study participants.

FIGS. 25A-25C are photographs showing kidneys of non-obese medium dose (10 mg/Kg) study participants. In particular, FIG. 25A shows a kidney of a naïve specimen, FIG. 25B shows a kidney of a control specimen, and FIG. 25C shows a kidney of an M4 specimen.

Non-Obese High Dose Study Results

Figure 26:
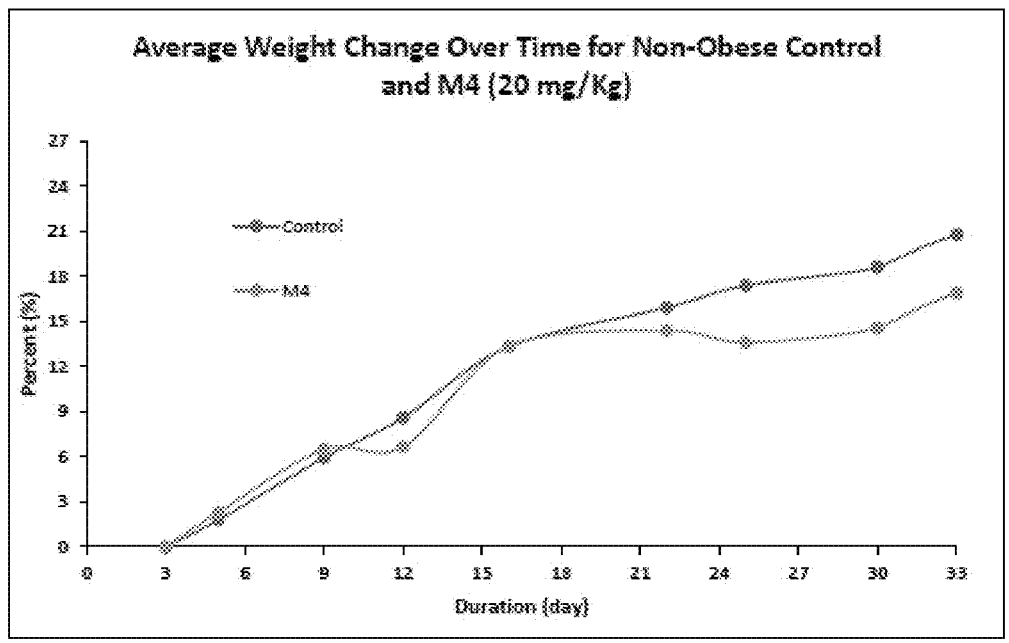

FIG. 26 illustrates the average weight change over time for the non-obese high dose (20 mg/Kg) control group and test group during days 1-33 of the study. As shown in FIG. 26, both the control group and the group treated with M4 exhibited a positive weight change from day 3-33. Overall, M4 seems to exhibit a lower average weight change pattern compared to the control. At the end of the treatment period, non-obese participants injected with control had 3.89% larger change in weight as compared to those injected with M4.

Figure 27:
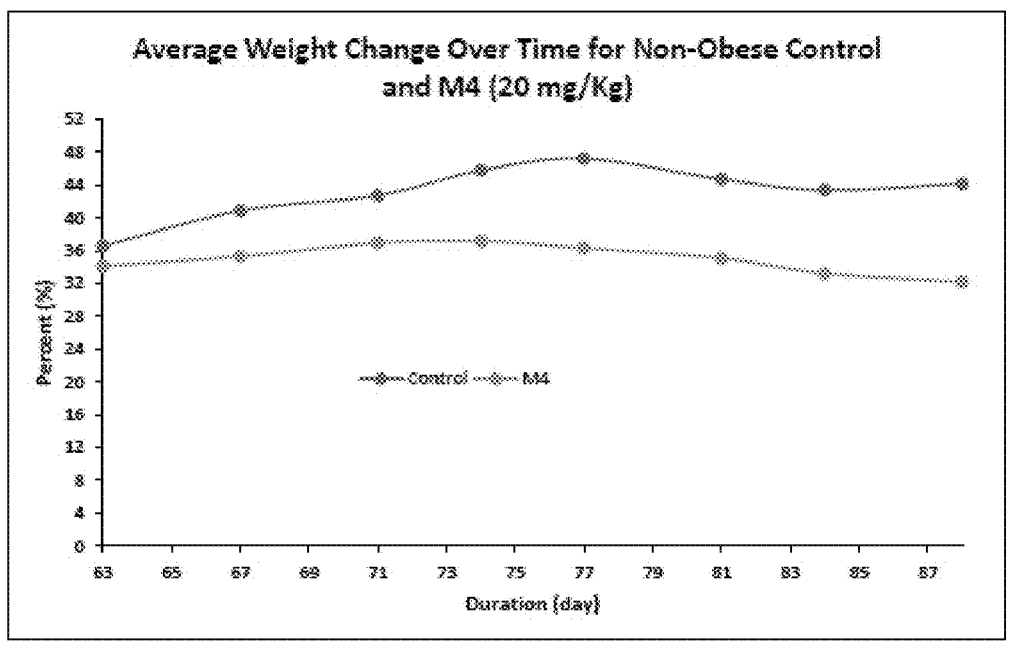

FIG. 27 illustrates the average weight change of these study participants during days 63-88 of the study.

Figures 28A, 28B:
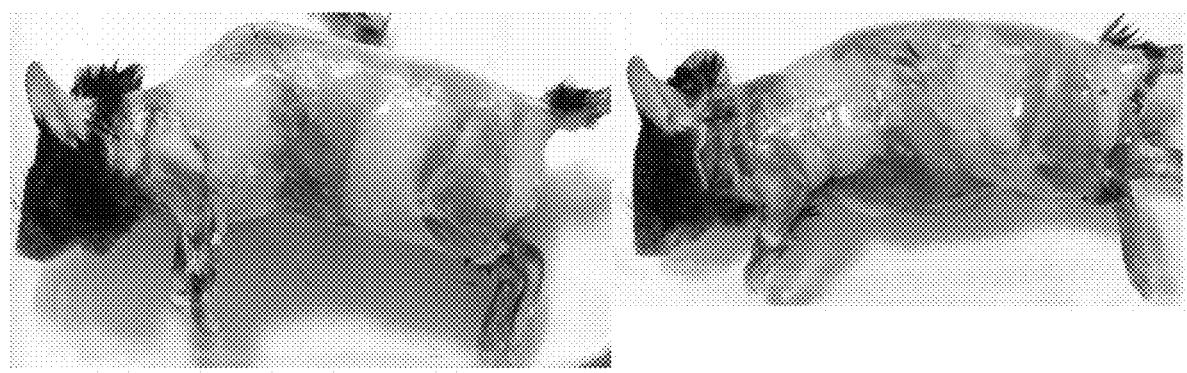

FIGS. 28A and 28B are photographs of the subcutaneous fat of non-obese test and control participants given the high dose (20 mg/Kg) treatment in the study. FIG. 28A shows the control participant and FIG. 28B shows the M4 participant.

Figure 29:
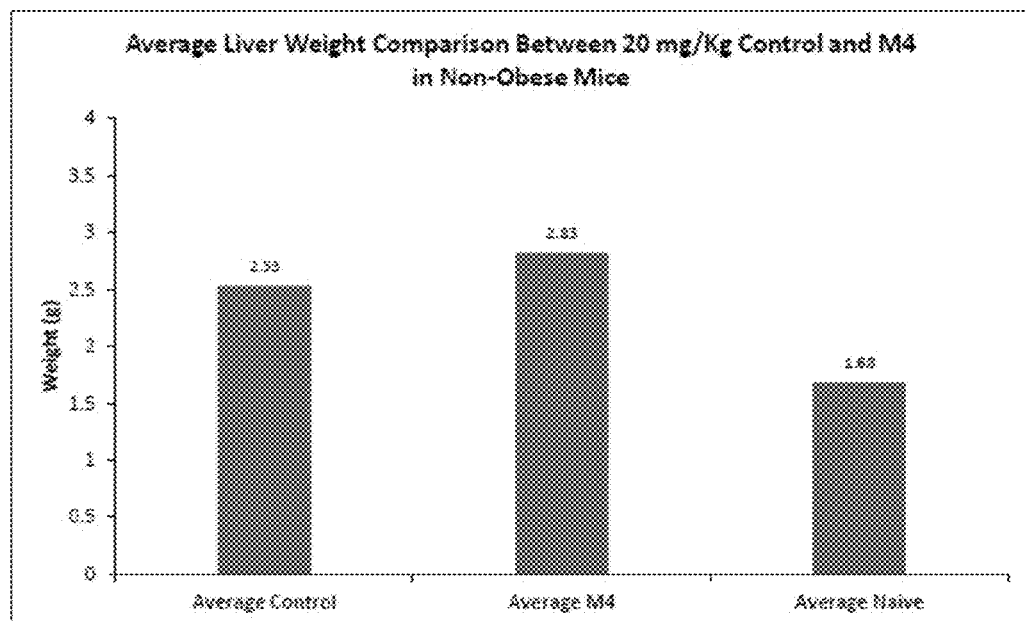

FIG. 29 is a chart showing average liver weight for non-obese high dose (20 mg/Kg) study participants.

Figures 30A, 30B, 30C:
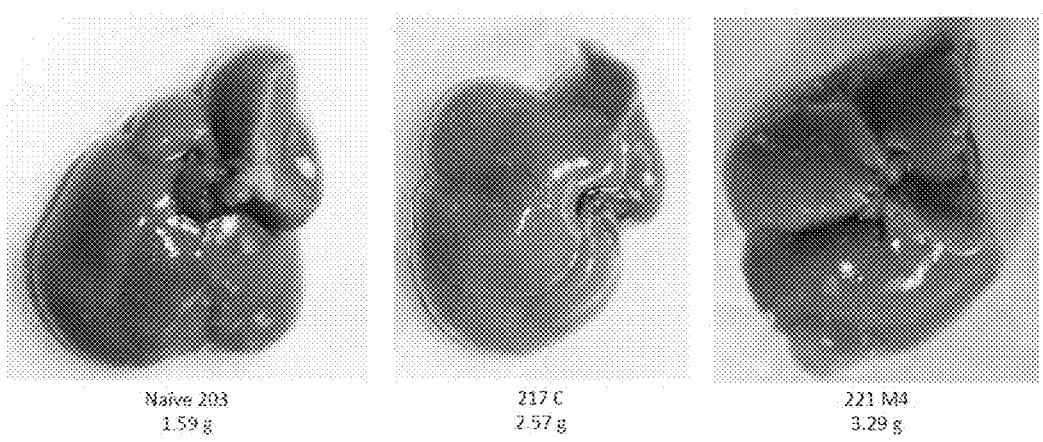

FIGS. 30A-30C are photographs of the livers of non-obese high dose study participants. In particular, FIG. 30A shows the liver of a naïve mouse, FIG. 30B shows the liver of a control mouse, and FIG. 30C shows the liver of a mouse treated with M4.

FIG. 31 is a chart illustrating average heart weight for non-obese study participants who received a high dose (20 mg/Kg) treatment.

FIGS. 32A-32C are photographs showing the hearts of high dose study participants. In particular, FIG. 32A shows the heart of a naïve mouse, FIG. 32B shows the heart of a control mouse, and FIG. 32C shows the heart of a mouse treated with M4.

FIG. 33 is a chart illustrating average subcutaneous fat for non-obese high dose (20 mg/Kg) study participants.

Figure 34A:
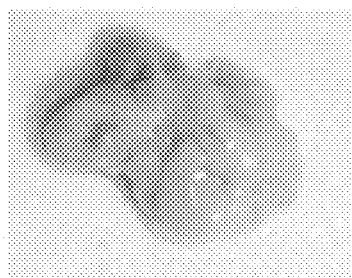
Figure 34B:
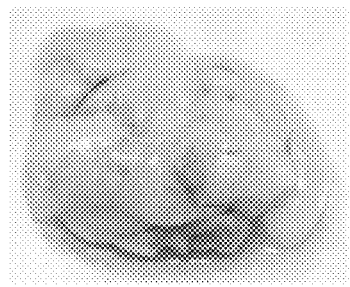
Figure 34C:
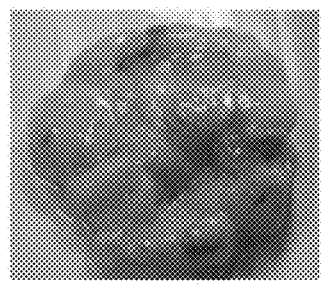

FIGS. 34A-34C are photographs showing subcutaneous fat of non-obese high dose (20 mg/Kg) study participants. In particular, FIG. 34A shows subcutaneous fat of a naïve specimen, FIG. 34B shows subcutaneous fat of a control specimen, and FIG. 34C shows subcutaneous fat of an M4 specimen.

Figure 35:
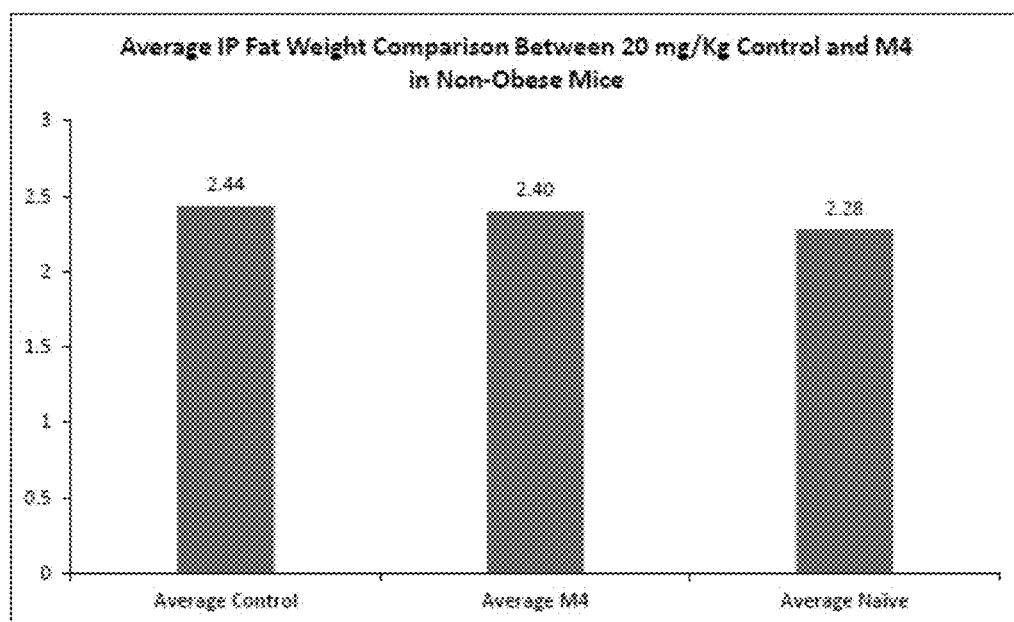

FIG. 35 is a chart showing average IP fat for non-obese high dose (20 mg/Kg) study participants.

Figure 36A:
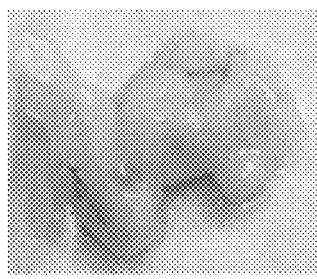
Figure 36B:
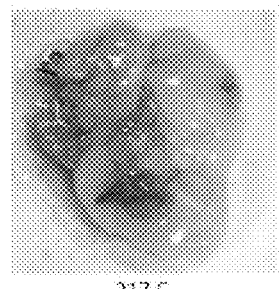
Figure 36C:
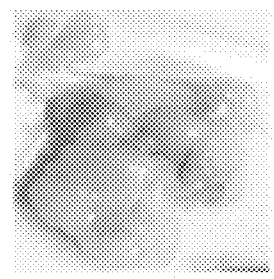

FIGS. 36A-36C are photographs showing IP fat of non-obese high dose (20 mg/Kg) study participants. In particular, FIG. 36A shows IP fat of a naïve specimen, FIG. 36B shows IP fat of a control specimen, and FIG. 36C shows IP fat of an M4 specimen.

Figure 37:
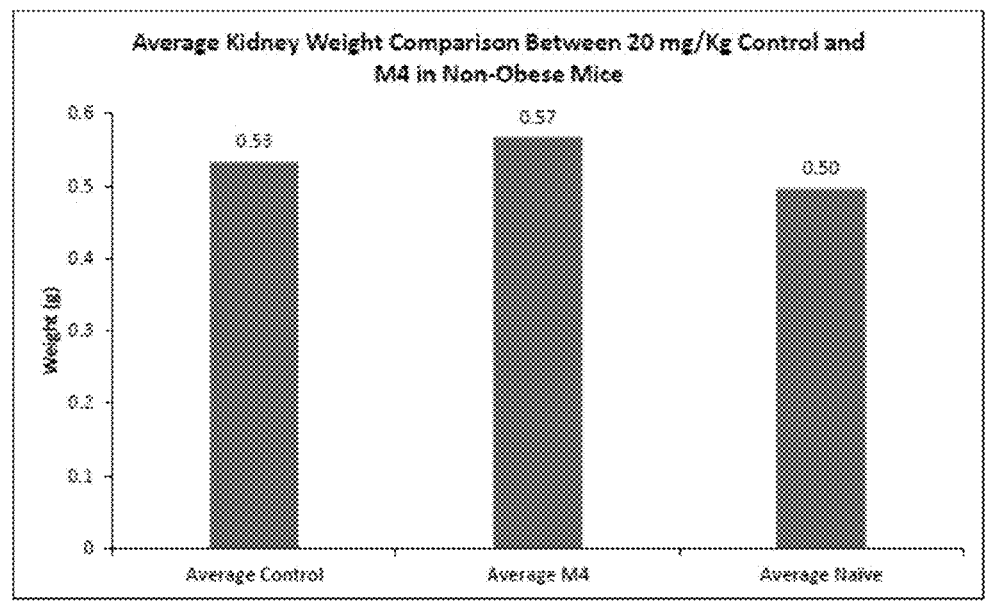

FIG. 37 is a chart of average kidney weight in non-obese high dose (20 mg/Kg) study participants.

Figure 38A:
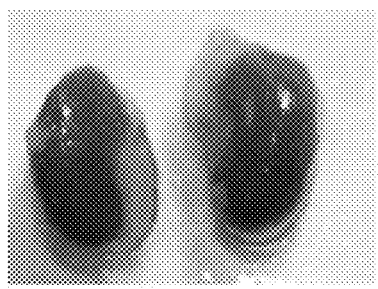
Figure 38B:
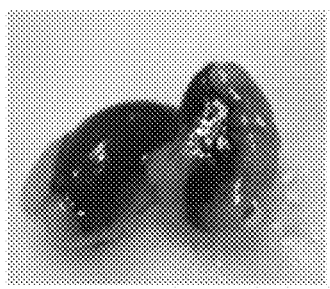
Figure 38C:
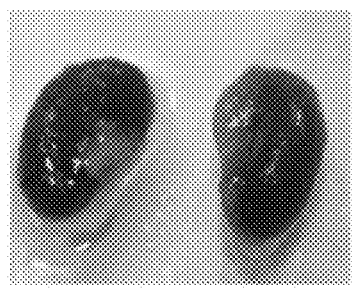

FIGS. 38A-38C are photographs showing kidneys of non-obese high dose (20 mg/Kg) study participants. In particular, FIG. 38A shows a kidney of a naïve specimen, FIG. 38B shows a kidney of a control specimen, and FIG. 38C shows a kidney of an M4 specimen.

Obese Low Dose Study Results

Figure 39:
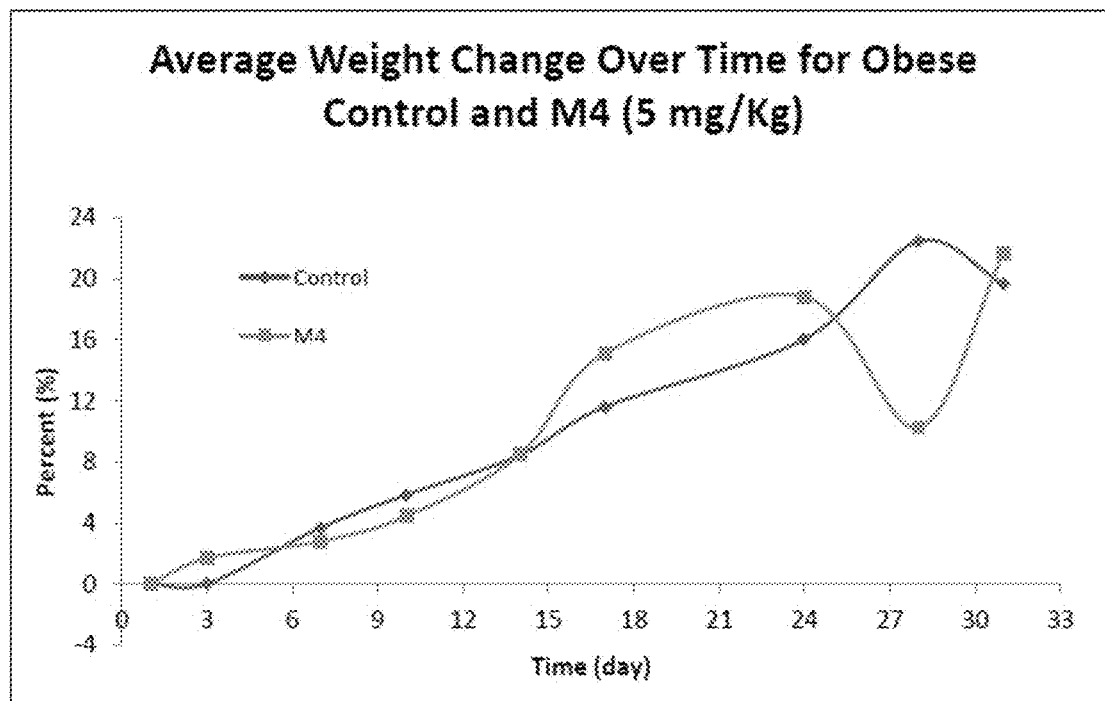

FIG. 39 illustrates the average weight change over time for the obese low dose (5 mg/Kg) control group and test group during days 1-33 of the study. As shown in FIG. 39, the obese control exhibited a gradual increasing weight trend for 31 days. M4 displays the same trend with a large percent increase in weight from days 14-24 and a large decrease in weight on day 28. At the end of the treatment time period, obese models who were injected with 5 mg/Kg of the control had 2.02% smaller change in weight compared to those treated with M4.

Figure 40:
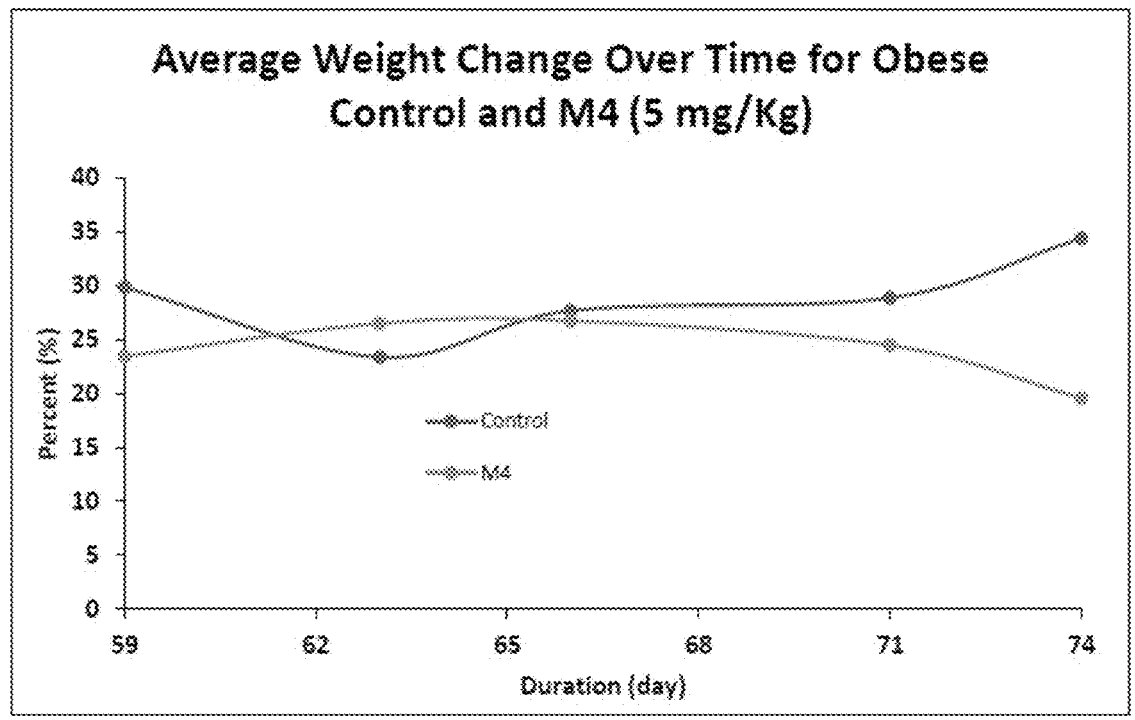

FIG. 40 illustrates the average weight change over time for the obese low dose (5 mg/Kg) control group and the group treated with M4 during days 59-74 of the study.

FIGS. 41A and 41B are photographs of the subcutaneous fat of obese test and control participants given the low dose (5 mg/Kg) treatment in the study. FIG. 41A shows the control participant and FIG. 41B shows the M4 participant.

FIG. 42 is a chart showing average liver weight for obese low dose (5 mg/Kg) study participants.

FIGS. 43A-43C are photographs of the livers of obese low dose study participants. In particular, FIG. 43A shows the liver of a naïve mouse, FIG. 43B shows the liver of a control mouse, and FIG. 43C shows the liver of a mouse treated with M4.

FIG. 44 is a chart illustrating average heart weight for obese study participants who received a low dose (5 mg/Kg) treatment.

FIGS. 45A-45C are photographs showing the hearts of low dose obese study participants. In particular, FIG. 45A shows the heart of a naïve mouse, FIG. 45B shows the heart of a control mouse, and FIG. 45C shows the heart of a mouse treated with M4.

FIG. 46 is a chart showing average IP fat of obese low dose (5 mg/Kg) study participants.

FIGS. 47A-47C are photographs showing IP fat of obese low dose (5 mg/Kg) study participants. In particular, FIG. 47A shows IP fat of a naïve specimen, FIG. 47B shows IP fat of a control specimen, and FIG. 47C shows IP fat of an M4 specimen.

FIG. 48 is a chart of average kidney weight in obese low dose (5 mg/Kg) study participants.

FIGS. 49A-49C are photographs showing kidneys of obese low dose (5 mg/Kg) study participants. In particular, FIG. 49A shows kidneys of a naïve specimen, FIG. 49B shows kidneys of a control specimen, and FIG. 49C shows kidneys of an M4 specimen.

Obese Medium Dose Study Results

Figure 50:
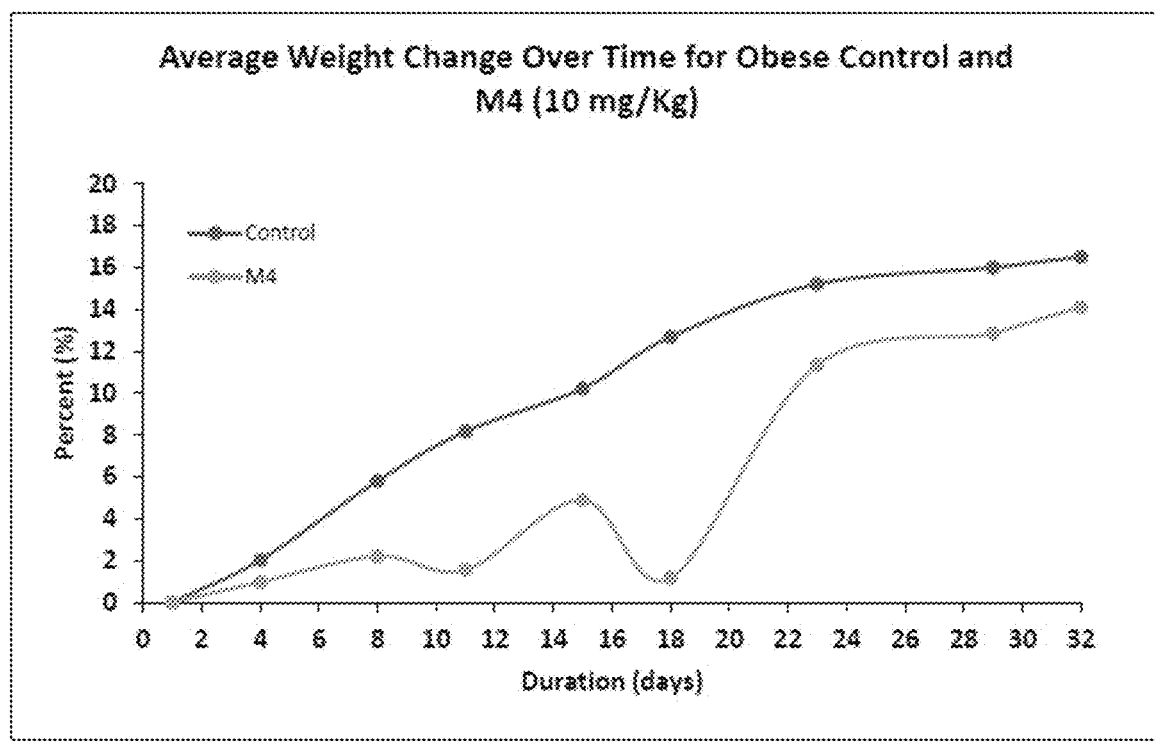

FIG. 50 illustrates the average weight change over time for the obese medium dose (10 mg/Kg) control group and test group during days 1-32 of the study. As shown in FIG. 50, the obese control exhibited a gradual increasing weight trend for 31 days. M4 displays the same trend with fluctuations between days 8 and 18. The fluctuations cease after day 18 and exhibit a large increase thereafter. At the end of the treatment time period, obese models who were injected with 10 mg/Kg of the control had 2.02% smaller change in weight compared to those treated with M4.

Figure 51:
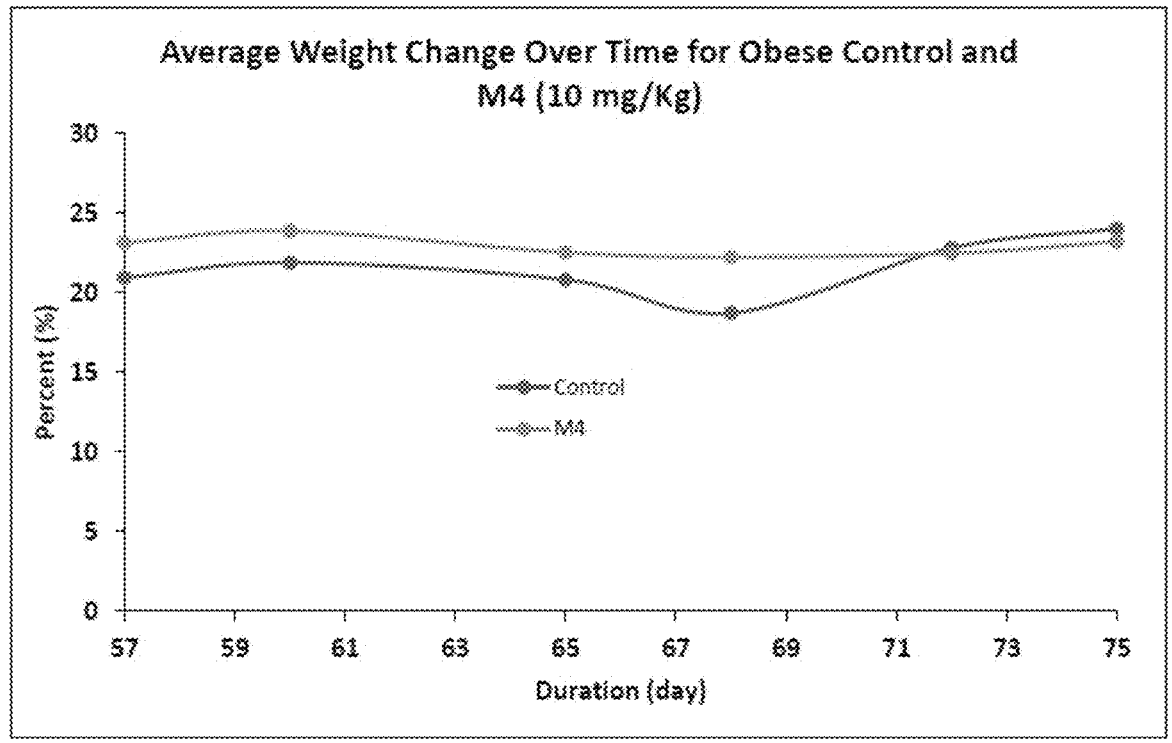

FIG. 51 illustrates the average weight change over time for the obese medium dose (10 mg/Kg) control group and the group treated with M4 during days 57-75 of the study.

FIGS. 52A and 52B are photographs of subcutaneous fat of obese test and control participants given the medium dose (10 mg/Kg) treatment in the study. FIG. 52A shows the control participant, and FIG. 52B shows the M4 participant.

FIG. 53 is a chart showing average liver weight for obese medium dose (10 mg/Kg) study participants.

FIGS. 54A-54C are photographs of the livers of obese medium dose study participants. In particular, FIG. 54A shows the liver of a naïve mouse, FIG. 54B shows the liver of a control mouse, and FIG. 54C shows the liver of a mouse treated with M4.

Figure 55:
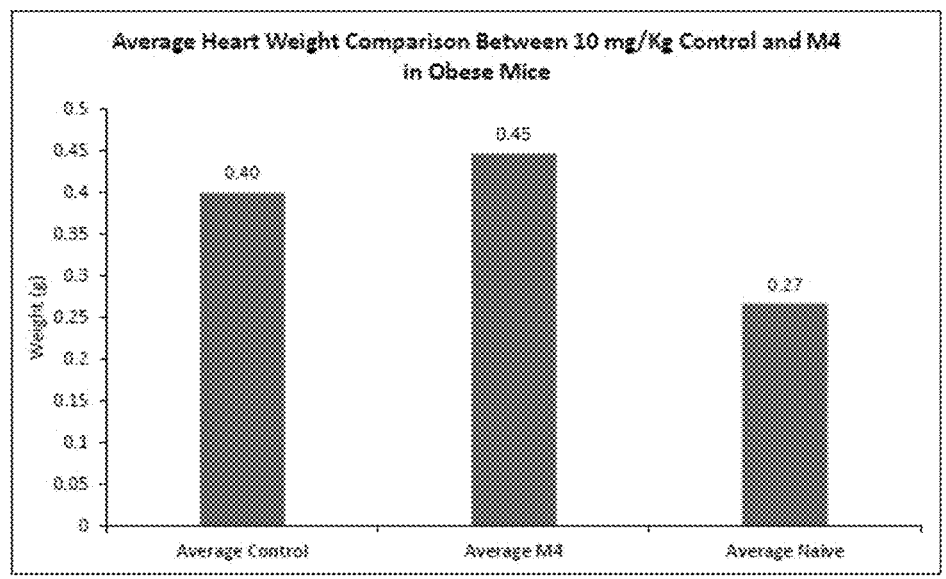

FIG. 55 is a chart illustrating average heart weight for obese study participants who received a medium dose (10 mg/Kg) treatment.

Figure 56A:
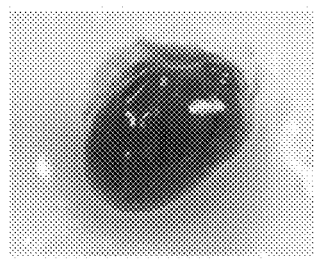
Figure 56B:
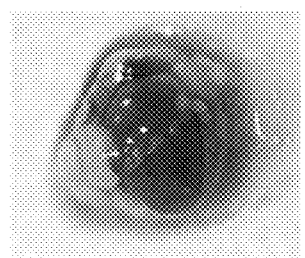
Figure 56C:
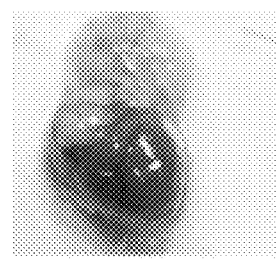

FIGS. 56A-56C are photographs showing the hearts of medium dose obese study participants. In particular, FIG. 56A shows the heart of a naïve mouse, FIG. 56B shows the heart of a control mouse, and FIG. 56C shows the heart of a mouse treated with M4.

Figure 57:
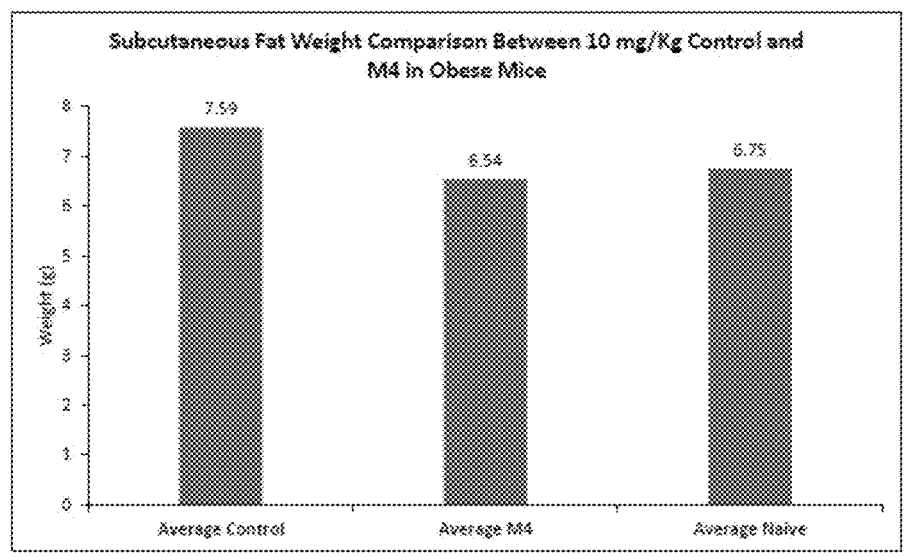

FIG. 57 is a chart illustrating average subcutaneous fat for obese medium dose (10 mg/Kg) study participants.

FIGS. 58A-58C are photographs showing subcutaneous fat of obese medium dose (10 mg/Kg) study participants. In particular, FIG. 58A shows subcutaneous fat of a naïve specimen, FIG. 58B shows subcutaneous fat of a control specimen, and FIG. 58C shows subcutaneous fat of an M4 specimen.

FIG. 59 is a chart showing average IP fat of obese medium dose (10 mg/Kg) study participants.

FIGS. 60A-60C are photographs showing IP fat of obese medium dose (10 mg/Kg) study participants. In particular, FIG. 60A shows IP fat of a naïve specimen, FIG. 60B shows IP fat of a control specimen, and FIG. 60C shows IP fat of an M4 specimen.

Figure 61:
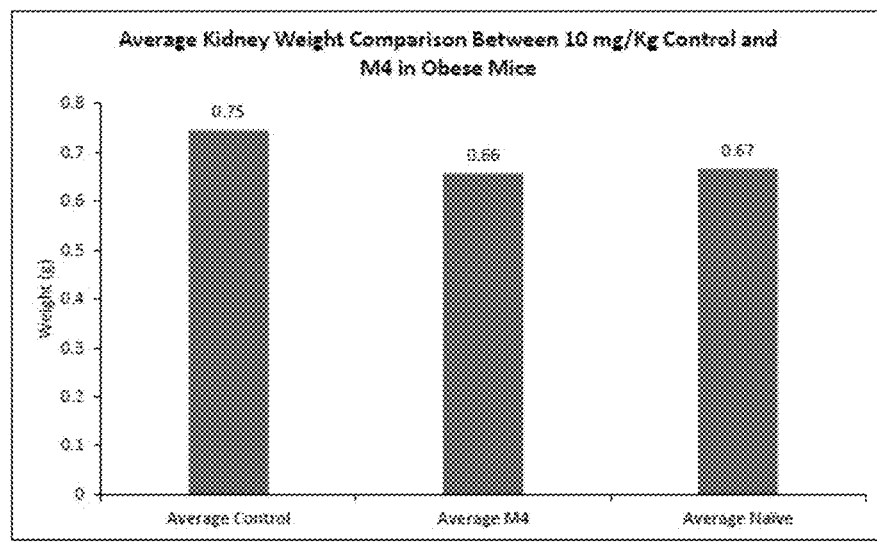

FIG. 61 is a chart of average kidney weight in obese medium dose (10 mg/Kg) study participants.

Figures 62A, 62B, 62C:
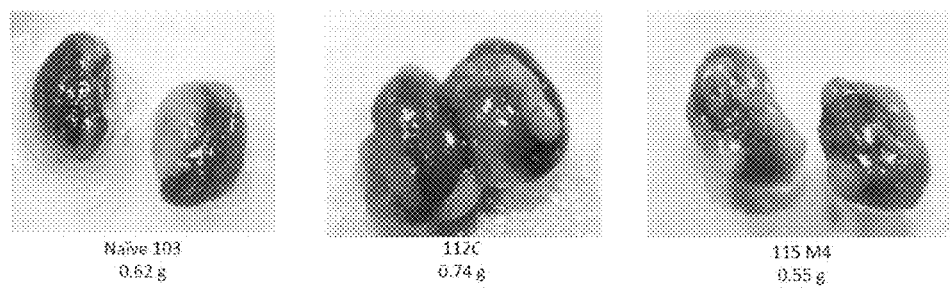

FIGS. 62A-62C are photographs showing kidneys of obese medium dose (10 mg/Kg) study participants. In particular, FIG. 62A shows kidneys of a naïve specimen, FIG. 62B shows kidneys of a control specimen, and FIG. 62C shows kidneys of an M4 specimen.

Obese High Dose Study Results

Figure 63:
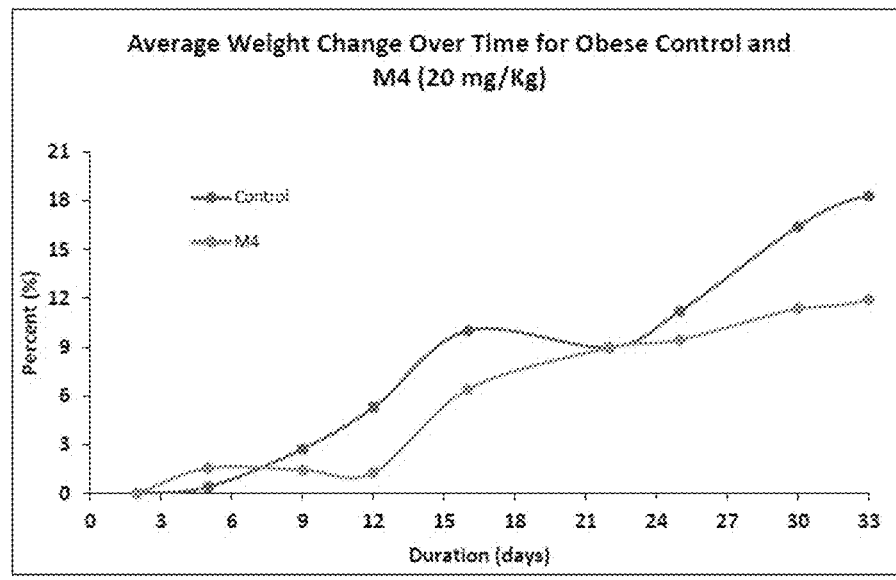

FIG. 63 illustrates the average weight change over time for the obese high dose (20 mg/Kg) control group and test group during days 1-33 of the study. As shown in FIG. 65, both the obese control and M4 groups exhibited a positive weight change. M4 displays a lower overall average. At the end of the treatment time period, obese models who were injected with 20 mg/Kg of M4 had 6.39% smaller change in weight compared to those treated with the control.

FIG. 64 illustrates the average weight change over time for the obese high dose (20 mg/Kg) control group and the group treated with M4 during days 63-81 of the study.

FIGS. 65A and 65B are photographs of subcutaneous fat of obese test and control participants given the high dose (20 mg/Kg) treatment in the study. FIG. 65A shows the control participant and FIG. 65B shows the M4 participant.

FIG. 66 is a chart showing average liver weight for obese high dose (20 mg/Kg) study participants.

FIGS. 67A-67C are photographs of the livers of obese high dose study participants. In particular, FIG. 67A shows the liver of a naïve mouse, FIG. 67B shows the liver of a control mouse, and FIG. 67C shows the liver of a mouse treated with M4.

FIG. 68 is a chart illustrating average heart weight for obese study participants who received a high dose (20 mg/Kg) treatment.

FIGS. 69A-69C are photographs showing the hearts of high dose obese study participants. In particular, FIG. 69A shows the heart of a naïve mouse, FIG. 69B shows the heart of a control mouse, and FIG. 69C shows the heart of a mouse treated with M4.

FIG. 70 is a chart showing average IP fat of obese high dose (20 mg/Kg) study participants.

FIGS. 71A-71C are photographs showing IP fat of obese high dose (20 mg/Kg) study participants. In particular, FIG. 71A shows IP fat of a naïve specimen, FIG. 71B shows IP fat of a control specimen, and FIG. 71C shows IP fat of an M4 specimen.

FIG. 72 is a chart of average kidney weight in obese high dose (20 mg/Kg) study participants.

Figure 73A:
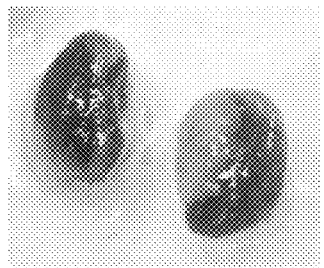
Figure 73B:
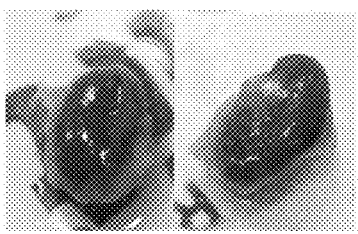
Figure 73C:
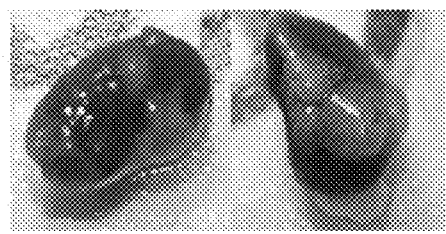

FIGS. 73A-73C are photographs showing kidneys of obese high dose (20 mg/Kg) study participants. In particular, FIG. 73A shows kidneys of a naïve specimen, FIG. 73B shows kidneys of a control specimen, and FIG. 73C shows kidneys of an M4 specimen. In summary, the murine study participants exhibited a 30% (average) fat loss. 25% of study participants gained muscle. There was no evidence of toxicity of the therapeutic agent(s). Reduced fatty liver infiltration was also noted for study participants. Effectiveness extending beyond treatment timeline was noted, such as greater than 6 months of effectiveness (20-50% of mice lifespan). Long-term prevention of metabolic syndrome was also noted.

Adipocyte Culture Models

The following experimentation was performed to determine the efficacy of M4 treatment on human adipocyte cells. In this experimentation, preadipocytes were obtained from Lonza Group (Lonza, Basel, Switzerland). The adipocytes were isolated from fat from normal, un-diseased donors.

Human preadipocyte cells, as opposed to human adipocytes, were used in the following experiment. The maintenance media used was preadipocyte growth medium-2 (PGM-2) plus supplements: preadipocyte basal medium (500 mL), FBS (10%), L-glutamine (2 mg/mL), GA-1000 (30 µg/mL). The differentiation media used was PGM-2 (100 mL), insulin (2 mg/mL), dexamethasone (0.2 mg/mL), indomethacin (0.4 mg/nL), isobutyl-methylxanthine (0.2 mg/nL).

Primary human preadipocytes were pre-plated in 6 well plates and induced to become adipocytes. The adipocytes were then exposed to 0.08 mg/mL experimental compound or a control vehicle for 14 days. The resulting cells were analyzed by phase contrast microscopy set to identify lipid engorged cells, MTT (viability), a cell staining.

Figure 74A:
Figure 74B:
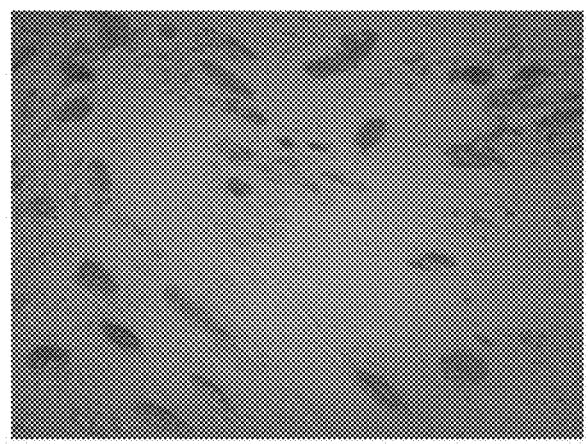

FIGS. 74A-74B show images of control human adipocyte cultures obtained with light microscopy. In particular, FIG. 74A shows a culture at high magnification and FIG. 74B shows the same culture at low magnification. Lipid engorged and non-engorged human adipocytes can be seen in FIGS. 74A-74B.

Figure 75A:
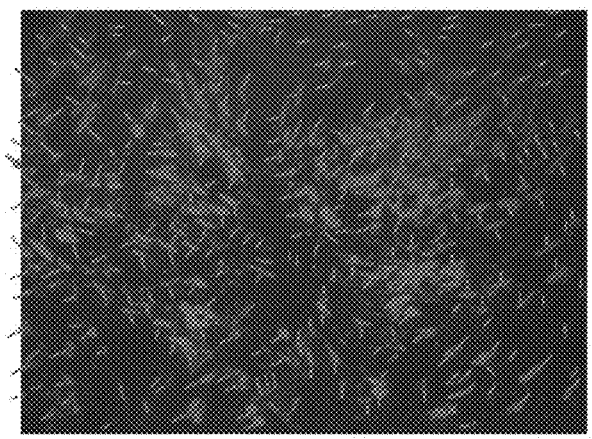
Figure 75B:

FIGS. 75A and 75B show images of human adipocyte cultures having lipid engorged adipocytes. The images shown in FIGS. 75A and 75B were obtained using low magnification phase contrast microscopy. FIG. 75A shows cells exposed to a control and FIG. 75B shows cells exposed to M4. As shown in FIGS. 75A and 75B, significantly more lipid engorged adipocytes are present in the control sample as compared to the sample treated with the experimental compound.

Figure 76A:
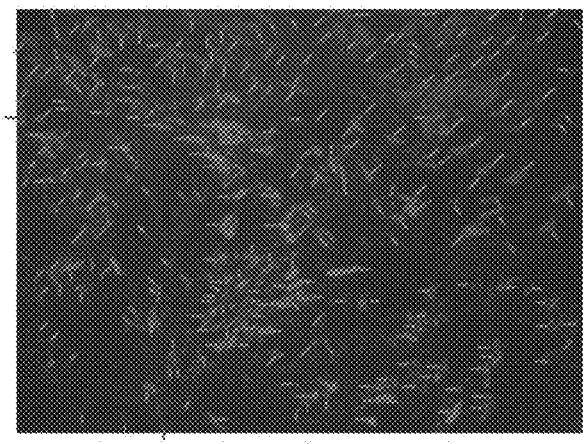
Figure 76B:

FIGS. 76A and 76B show images of human adipocyte cultures having lipid engorged adipocytes. The images shown in FIGS. 76A and 76B were obtained using low magnification phase contrast micrographs. FIG. 76A shows cells exposed to a control and FIG. 76B shows cells exposed to M4. As shown in FIGS. 76A and 76B, significantly more lipid engorged adipocytes are present in the control sample as compared to the sample treated with the experimental compound.

Figure 77A:
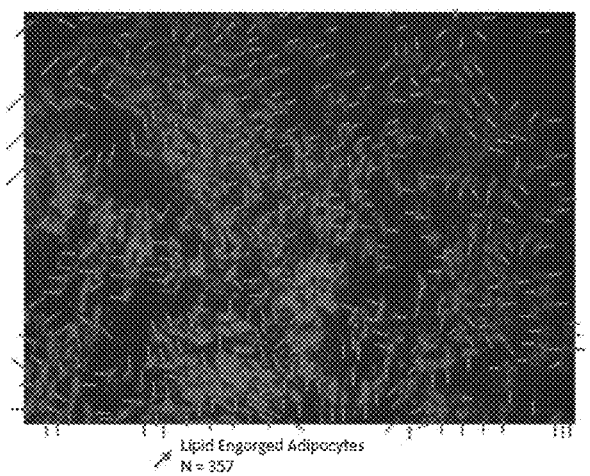
Figure 77B:
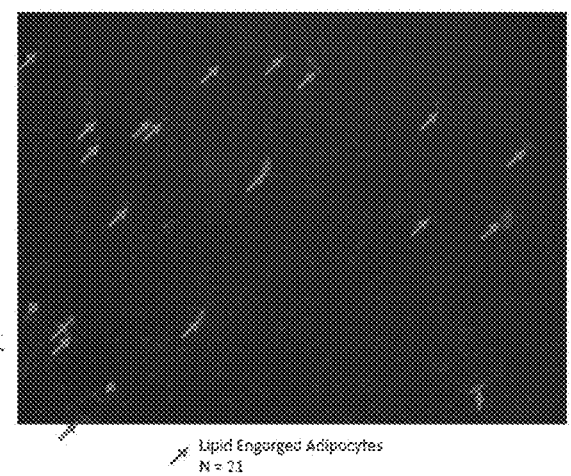

FIGS. 77A and 77B show images of human adipocyte cultures having lipid engorged adipocytes. The images shown in FIGS. 77A and 77B were obtained using low magnification phase contrast micrographs. FIG. 77A shows cells exposed to a control and FIG. 77B shows cells exposed to M4. As shown in FIGS. 77A and 77B, significantly more lipid engorged adipocytes are present in the control sample as compared to the sample treated with the experimental compound.

Figure 78A:
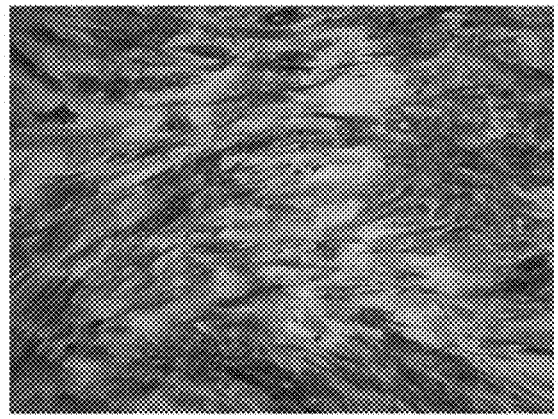
Figure 78B:
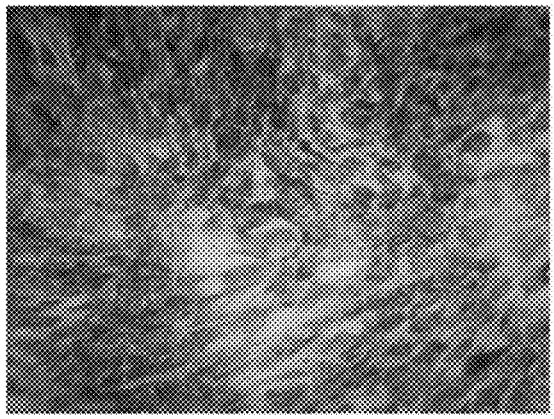

FIGS. 78A and 78B show images of human adipocyte cultures obtained using crystal violet stain (DNA and protein stain). FIG. 78A shows cells exposed to a control and FIG. 78B shows cells exposed to M4. The similar number of cells shown in FIGS. 78A and 78B suggests the difference in the number of lipid engorged cells is not a result of cytotoxicity.

FIGS. 79A and 79B are images of human adipocytes obtained by MTT to approximate reduced cofactor NADH/NADPH levels. FIG. 79A shows cells exposed to a control and FIG. 79B shows cells exposed to M4. As shown in FIGS. 79A and 79B, both adipocyte populations are viable and there are slightly higher concentrations of reduced nucleotides in the control sample.

FIG. 80 is a chart showing quantitative MTT results as measured for control samples and M4 samples. As shown in FIG. 80, the control cells have slightly higher levels of NADH/NADPH. Without wishing to be bound by theory, M4 treatment may reduce the level of white fat in a patient, possibly replacing some or all of the white fat with brown fat. As brown fat uses up reduced cofactors to generate heat, reduced levels of these cofactors when there are the same number of cells may indicate that white adipocytes are converted to brown adipocytes during treatment with M4.

These experimental results show there are fewer lipid engorged adipocytes after treatment with the experimental compound, M4. Additionally, the total number of cells are similar in control and in treatment groups, which indicates low toxicity of M4. Furthermore, there is less reduced cofactor related MTT reduction in the treatment group, which is consistent with "leaky" brown fat cells.

What is claimed is:

1. A method for treatment of obesity and obesity-related metabolic diseases in animals which method comprises increasing the animal's metabolic function by administering to the animal a therapeutically effective amount of an antisense oligonucleotide, wherein the antisense olignucleotide has a structure defined by the following formula:

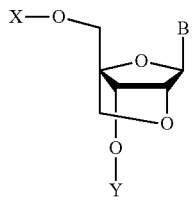

wherein B is a pyrimidine or purine nucleic acid base, an analogue thereof, X and Y are identical or different, and each represents a hydrogen atom, an alkyl group, an alkenyl group, an alkynyl group, a cycloalkyl group, an aralkyl group, an aryl group, an acyl group, or a silyl group, or an amidite derivative thereof, and wherein B includes the following sequence:

5'GTTGAGATAGCATCAG-3' (SEQ ID NO: 1).

2. The method of claim 1, wherein the therapeutic agent is administered orally, parenterally, topically, directly to the lungs, rectally or vaginally.

3. The method of claim 1, wherein the antisense oligonucleotide is administered in a dose of between 1 mg/kg and 20 mg/kg based on the patient's weight in kg.

4. The method of claim 3, wherein the dose is administered once, twice or, three time or more per day.

5. The method of claim 3, wherein treatment is continued daily for 30, 45, 60 or 90 days.

6. The method of claim 1, wherein the animal is a human, and the disease is selected from the group consisting of nonalcoholic fatty liver disease, metabolic syndrome, Duchenne muscular dystrophy (DMD), diabetes, cancer recovery, muscle loss due to deconditioning, hypertension, nonalcoholic steatohepatitis (NASH), dyslipidemia and obesity.

7. A therapeutic formulation for treatment of obesity, and obesity-related metabolic diseases comprising an antisense oligonucleotide in a pharmaceutically acceptable carrier therefor, wherein the antisense oligonucleotide has a structure defined by the following formula:

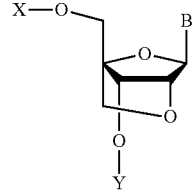

wherein B is a pyrimidine or purine nucleic acid base, an analogue thereof, X and Y are identical or different, and each represents a hydrogen atom, an alkyl group, an alkenyl group, an alkynyl group, a cycloalkyl group, an aralkyl group, an aryl group, an acyl group, or a silyl group, or an amidite derivative thereof, and wherein B includes the following sequence:

5'GTTGAGATAGCATCAG-3' (SEQ ID NO: 1).

8. The formulation of claim 7, wherein the therapeutic agent is in a pharmaceutically acceptable carrier selected form the group consisting of a tablet, capsule, liquid, solution, suspension, syrup, elixir, cream, ointment, lotion, gel, patch, dry powder and suppository.

9. The formulation of claim 7, wherein the antisense oligonucleotide is in an unit dosage form.

10. The formulation of claim 7, wherein the disease is selected from the group consisting of nonalcoholic fatty liver disease, metabolic syndrome, Duchenne muscular dystrophy (DMD), diabetes, cancer recovery, muscle loss due to deconditioning, hypertension, nonalcoholic steatohepatitis (NASH), dyslipidemia and obesity.

* * * * *

SEQUENCE LISTING

```
<160> NUMBER OF SEQ ID NOS: 1

<210> SEQ ID NO 1
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 1
gttgagatag catcag                                                16
```